(12) United States Patent
Saaristo et al.

(10) Patent No.: US 8,852,936 B2
(45) Date of Patent: Oct. 7, 2014

(54) AUTOLOGOUS LYMPH NODE TRANSFER IN COMBINATION WITH VEGF-C OR VEGF-D GROWTH FACTOR THERAPY TO TREAT LYMPHEDEMA AND TO IMPROVE RECONSTRUCTIVE SURGERY

(71) Applicant: Laurantis Pharma Oy, Turku (FI)

(72) Inventors: Anne Saaristo, Turku (FI); Kari Alitalo, Helsinki (FI)

(73) Assignee: Laurantis Pharma Oy, Turku (FI)

( * ) Notice: Subject to any disclaimer, the term of this patent is extended or adjusted under 35 U.S.C. 154(b) by 0 days.

(21) Appl. No.: 13/624,145

(22) Filed: Sep. 21, 2012

(65) Prior Publication Data

US 2014/0087002 A1   Mar. 27, 2014

(51) Int. Cl.
  *C12N 5/071* (2010.01)
  *A61F 2/00* (2006.01)
(52) U.S. Cl.
  USPC ............ 435/372; 435/325; 424/423; 424/578
(58) Field of Classification Search
  None
  See application file for complete search history.

(56) References Cited

U.S. PATENT DOCUMENTS

2008/0267924 A1 * 10/2008 Alitalo et al. ............... 424/93.7
2012/0125348 A1    5/2012 Alitalo et al.

FOREIGN PATENT DOCUMENTS

WO    WO 2005011722 A2 *  2/2005   ............ A61K 38/00

OTHER PUBLICATIONS

Saaristo, A. et al. "Lymph Node Transfer and Growth Factor Therapy for Lymphedema Patients" 23rd *International Congress of Lymphology*, Sep. 20, 2011.

* cited by examiner

*Primary Examiner* — Sharmila Landau
*Assistant Examiner* — Douglas F White
(74) *Attorney, Agent, or Firm* — Saliwanchik, Lloyd & Eisenschenk

(57) ABSTRACT

Materials and methods are provided to improve survival of lymph nodes and integration of lymph nodes into a lymphatic network, following lymph node transplantation. The treatment or prevention of lymphedema is also addressed. A method of lymph node transfer includes transferring or transplanting a lymph node or lymph node fragment in a mammalian subject; and administering a composition comprising an agent selected from the group consisting of Vascular Endothelial Growth Factor C (VEGF-C) polynucleotides, VEGF-C polypeptides, Vascular Endothelial Growth Factor D (VEGF-D) polynucleotides, and VEGF-D polypeptides to a perinodal site within 20 cm of the lymph node or lymph node fragment. In certain embodiments, the agent is present in the composition in an amount effective to promote survival of the lymph node and integration of the lymph node into a lymphatic network in the mammalian subject, at the site of transfer or transplantation.

28 Claims, 7 Drawing Sheets

Comparison of oedema accumulation following intranodal or perinodal injection

Comparison of % fat and fibrosis following intranodal or perinodal injection

For absolute data the % fat and fibrosis was calculated as: (100 × Total combined area of fat and fibrosis of five slides)/(Total area of the five slides)

Comparison of lymph node size following intranodal or perinodal injection

Comparison of number of lymph vessels following intranodal or perinodal injection Comparison of number of PECAM-1 positive capillaries following intranodal or perinodal injection Comparison of number of PROX-1 positive vessels following intranodal or perinodal injection Comparison of number of VEGFR-3 positive capillaries following intranodal or perinodal injection

AUTOLOGOUS LYMPH NODE TRANSFER IN COMBINATION WITH VEGF-C OR VEGF-D GROWTH FACTOR THERAPY TO TREAT LYMPHEDEMA AND TO IMPROVE RECONSTRUCTIVE SURGERY

FIELD OF THE INVENTION

The present invention generally relates to materials and methods to improve healing of skin and underlying tissue following a surgical procedure.

BACKGROUND

Lymphedema is a debilitating condition characterized by chronic tissue edema and impaired immunity. At present, no curative treatment is available for lymphedema patients, as current practice involves palliative care only. The principal cause of lymphedema in industrialized is surgery or radiation therapy of the armpit region to eradicate breast cancer metastases. Skin flap survival following surgical procedures, especially reconstructive surgical procedures, is often compromised by, among other complications, infection, ischemia and tissue edema. Tissue and skin flap breakdown remain a major problem in plastic surgery, especially in patients suffering from diabetic microangiopathy or other forms of peripheral vascular disease. In such patients wound healing is often delayed and defective and in these patients complications may lead to necrosis and eventually require costly and painful secondary surgical procedures.

The vascular endothelial growth factor (VEGF) family currently includes six members, which are important regulators of angiogenesis and lymphangiogenesis: VEGF, placenta growth factor (PlGF), VEGF-B, VEGF-C, VEGF-D, and VEGF-E. VEGF is also known as vascular permeability factor, and it is more potent than histamine in increasing capillary permeability to plasma proteins. VEGF binds selectively and with high affinity to receptor tyrosine kinases VEGFR-1 and VEGFR-2. Angiopoietins (Angs) constitute another family of endothelial growth factors that are ligands for the endothelium-specific receptor tyrosine kinase, Tie-2 (Tek). Although Angs do not appear to induce new vessel growth, they may be involved in vessel stabilization. Vascular permeability induced by VEGF, for example, is reported to be blocked by angiopoietin-1 (Ang-1).

The lymphatic vasculature transports fluid and macromolecules from tissues back to the blood circulation and links tissue fluids to lymph nodes as an immune surveillance system. Metastatic tumor cells frequently spread via the lymphatic vascular system and colonize lymph nodes. Breast cancer and melanoma in particular frequently spread to lymph nodes, necessitating radical surgery that destroys lymphatic vessel network and leads to impairment of afferent lymphatic flow. Approximately 20-30% of patients that have undergone radical axillary lymph node dissection develop lymphedema later on. Lymphedema is a progressive disease characterized by gross swelling of the affected limb, accompanied by fibrosis and susceptibility to infections.

Damage to the collecting lymphatic vessels causes the vast majority of all lymphedemas, and it has been estimated that several million patients suffer from such acquired lymphedema in the USA alone. In contrast, Milroy disease and other rare hereditary forms of lymphedema are caused by defects in lymphatic capillaries. Tyrosine kinase-inactivating point mutations of the VEGFR3 gene have been identified as a major cause of Milroy disease, and VEGF-C therapy has shown promising efficacy in preclinical animal models. However, previous work has only demonstrated lymphatic capillary reconstitution, whereas effects on the collecting lymphatic vessels that are more commonly damaged in lymphedema have not been addressed.

It has been reported that autologous lymph node transfer appears to have a favorable and persistent effect on postmastectomy lymphedema in humans. Lymph node transplantation may be used to treat limb lymphedema with other procurement sites such as cervical or auxiliary being possible.

Lymphatic vasculature plays a key role in the maintenance of tissue fluid homeostasis by collecting and draining extravasated fluid and macromolecules back to the blood circulation. The lymphatic system also has a major role in immune defence. Therefore, lymphatic vessels and lymph nodes are involved in several human diseases, such as lymphoedema, inflammation and tumour metastasis. The lymphatic capillaries in the peripheral tissues merge with larger collecting lymphatic vessels, specialized for the transport of large volumes of lymph, and connect with chains of lymph nodes. Chronic lymphoedema, caused commonly by infection and surgical or radiation therapy of metastatic cancer, remains a common clinical problem that lacks curative options. The effective treatment and staging of cancer often requires removal of regional lymph nodes and the associated collecting lymphatic vessels to eradicate metastases. This leads to a disruption in the lymphatic flow of the operated area, which frequently leads to lymphoedema of the affected limb. The conventional treatment for chronic lymphoedema aims at alleviating the symptoms and is mainly based on physiotherapy and/or controlled compression therapy, whereas surgical treatment options are limited. This is chiefly due to difficulties in identifying and preserving the lymphatic vessels even by modern microsurgical methods. Recently a microvascular lymph node transfer into axillas of patients that had undergone axillary lymph node dissection in response to disseminated breast cancer was shown to improve lymphatic drainage in some patients.

Understanding of the mechanism of lymphangiogenesis has increased considerably in recent years. Vascular endothelial growth factors (VEGFs) are important regulators of both angiogenesis and lymphangiogenesis. VEGFs stimulate cellular responses by binding to tyrosine kinase receptors (VEGFRs) that are specifically expressed in blood and lymphatic cells that line the luminal surface of vessels. VEGF-A binds to VEGF receptor-1 (VEGFR-1) and VEGFR-2 and induces mainly angiogenesis. VEGF-C and VEGF-D signalling via VEGFR-3 induce lymphangiogenesis. However, the proteolytically processed short forms of both VEGF-C and VEGF-D also bind to VEGFR-2, and have blood vascular effects in some tissues.

The treatment of lymphedema is currently based on physiotherapy, compression garments, and occasionally surgery.

US 2008-0267924 reports autologous lymph node transfer in combination with VEGF therapy, for the treatment of secondary lymphedema. The contents of US 2008-0267924 are hereby incorporated herein by reference.

US 2008-0267924 reports that intranodal administration of VEGF is preferred. All the relevant examples report intranodal administration. There is reference in the description to administration into "non-lymph node" tissue. However, this is not further defined.

BRIEF SUMMARY

The present invention addresses long-felt needs in the field of medicine by providing materials and methods to improve survival of lymph nodes and integration of lymph nodes into a lymphatic network, following lymph node transplantation. The use of this method in the treatment or inhibition of lymphedema is also addressed.

The invention provides a method of lymph node transfer comprising transferring or transplanting a lymph node or lymph node fragment in a mammalian subject; and administering a composition comprising an agent selected from the group consisting of Vascular Endothelial Growth Factor C (VEGF-C) polynucleotides, VEGF-C polypeptides, Vascular Endothelial Growth Factor D (VEGF-D) polynucleotides, and VEGF-D polypeptides to a perinodal site within 20 cm of the lymph node or lymph node fragment. In certain embodiments, the agent is present in the composition in an amount effective to promote survival of the lymph node and integration of the lymph node into a lymphatic network in the mammalian subject, at the site of transfer or transplantation.

"Transferring or transplanting a lymph node or lymph node fragment" refers to either transferring or transplanting an isolated lymph node or fragment, or transferring or transplanting tissue that contains the lymph node or fragment.

The invention provides the use of an agent selected from the group consisting of Vascular Endothelial Growth Factor C (VEGF-C) polynucleotides, VEGF-C polypeptides, Vascular Endothelial Growth Factor D (VEGF-D) polynucleotides, and VEGF-D polypeptides, for the manufacture of a medicament to improve lymph node transfer or transplantation.

In yet another embodiment, the invention provides a method of treating or inhibiting lymphedema in a mammalian subject comprising performing a lymph node transfer procedure on a mammalian that comprises transferring or transplanting a lymph node or lymph node fragment in the mammalian subject to a site at which the subject is experiencing lymphedema, or is at risk for lymphedema. Preferably, the lymphedema is secondary lymphedema. By "secondary lymphedema" is meant lymphedema caused by inflammatory or neoplastic obstruction of lymphatic vessels, and includes accumulation of ascites fluid due to peritoneal carcinomatosis or edema of the arm or other limbs following surgery or radiotherapy for breast cancer and other tumor types. Secondary lymphedema may also result from a trauma, a crush injury, hip or knee surgery, amputations, blood clots, vein grafts from cardiac surgery, chronic infections, or longstanding circulatory problems such as chronic venous insufficiency or diabetes. Secondary lymphedema may also be idiopathic in origin. The use of an agent described herein for the treatment of secondary lymphedema caused by any of the foregoing disorders is specifically contemplated.

In a preferred embodiment, the mammalian subject is human.

In a preferred embodiment, the administering of the composition defined above is to a perinodal site within 10 cm, most preferably 5 cm, of the lymph node fragment. Preferably, the perinodal site comprises perinodal fat tissue.

In a preferred embodiment, the administering of the composition is within a specified range, i.e. between a lower limit and an upper limit. Preferred lower limits are 0.5 mm, 1 mm, 2 mm, 3 mm, 4 mm, 5 mm, 10 mm, 15 mm and 20 mm. Preferred upper limits are 5 mm, 1 cm, 2 cm, 3 cm, 4 cm, 5 cm, 10 cm, 15 cm and 20 cm. Any of the aforementioned lower limits may be combined with any of the aforementioned upper limits.

In some embodiments, the invention involves transferring or transplanting at least one whole lymph node. In some variations, the lymph node is isogenic with the mammalian subject. In another variation, the lymph node is autologously transferred or transplanted from one location in the subject to another location in the same subject.

In one embodiment, the administration of the VEGF-C or VEGF-D is performed before the transferring or transplanting of the lymph node or lymph node fragment. Alternatively, the administration is performed or repeated after surgically removing the lymph node or lymph node fragment from one location and before the transferring or transplanting. In still another embodiment, the administration is performed or repeated after the transferring or transplanting of the lymph node or lymph node fragment. In certain exemplary embodiments, the lymph node transfer comprises transferring or transplanting a skin flap or skin graft in the mammalian subject, wherein the skin flap or skin graft comprises at least one lymph node or lymph node fragment. In a preferred embodiment, the skin flap or skin graft is a microvascular free-flap.

The procedure below is an exemplary lymph node transfer method:

Lymph Node Transfer Method:

Evaluation of the Lymphatic Vessel Function and Edema

Lymphedema symptoms are assessed pre- and postoperatively by upper limb volume measurements. The lymphatic vessel function of the upper limbs is visualized by isotopic lymphangiography (lymphoscintigraphy) both preoperatively and 6 and 12 months postoperatively.

Surgical Technique

Perforator vessels of the lymph node flap and breast reconstruction flap are preoperatively searched and marked using a doppler ultrasound device and angioCT imaging. A two-team approach is used enabling the simultaneous raising of the abdominal flap and preparation of the recipient vessels. As recipient vessels for microvascular anastomosis we use axillary thoracodorsal vessels in all patients. All scar tissue is removed from the axilla up to the level of the axillary vessels. Removal of the scar is continued wide along the axillary vessels and plexus until normal fat tissue is reached. All fibrotic and avascular tissue surrounding the vessels, nerves and muscles is dissected and adhesions released. We consider wide scar removal as an important step of the procedure.

For mastectomy patients with lymphedema symptoms a dual reconstruction flap is used to rebuild the both breast (BR flap) and lymph node anatomy (LN flap) in the axilla. Breast reconstruction flaps (DIEP or msTRAM flap) is raised as according to known techniques. The selected method is based on the anatomy: location, size and number of the perforator vessels in the lower abdominal wall. All breast reconstruction flaps are based on the inferior epigastric vessel pedicle from the contralateral inguinal area. The second lymph node flap (LN flap) contains lymphatic tissue: lymph nodes, lymphatic vessels and fat from the groin area surrounding the superficial circumflex iliac vessels (SCIA) or its perforators (see FIG. 1). The dual reconstruction flap, the LN-BR flap, also has dual blood vascular pedicles including the inferior epigastric artery/vein and the superficial circumflex iliac artery/vein.

The dissection is started with the preparation of the lymphatic tissue from the contralateral groin area. The quiescent lymph nodes are usually impalpable. To visualize lymphatic vessels and lymph nodes, 0.5 ml-1 ml of Patent Blue dye is injected intradermally into the lower lateral abdominal wall, just above the iliac crest. Five minutes after the Patent Blue injection, a skin incision is performed in the lower abdominal wall. The skin incision is located slightly lower than our normal DIEP/msTRAM flap incision and if needed, it is continued towards the lateral margin of the femoral artery.

Dissection is continued by identifying the superficial inferior epigastric vessels and the superficial circumflex iliac vein. The vessels and nodes draining the abdominal wall, which don't have direct connections to the inferior limb, are included in the flap with an abundant amount of surrounding fat tissue. Lymphatic tissue is identified by intradermal Patent Blue injection into the low lateral abdominal wall (above the crista iliaca). The flap is elevated laterally to the medial at the level of the muscular aponeurosis following the vascular pedicle, SCIA or its perforators. The lymphatic groin flap is left connected with the DIEP/msTRAM flap at the level of the superficial epigastric vessel pedicle. The superficial circumflex iliac artery and the vein is ligated at the level of their origin, and the superficial epigastric artery and vein (if identified in the flap) are ligated not in their origin but above the inguinal ligament. Any unnecessary dissection medial to femoral vessels is avoided. Next the normal DIEP/msTRAM flap is elevated according to known procedures. Blood perfusion into the tip of the lymphatic groin flap via the inferior epigastric vessel pedicle is evaluated just before ligation of this main pedicle.

The abdominal wall flap (DIEP or msTRAM flap) is then reshaped to reconstruct the missing breast. The previously prepared thoracodorsal vessels are ligated above the serratus branch, and the inferior epigastric vessels are anastomosed with the thoracodorsal vessels. Once the blood vascular anastomoses are performed the blood perfusion in the distal edge of the lymphatic groin flap is again evaluated. After that superficial circumflex iliac artery and vein are anastomosed with the retrograde thoracodorsal artery and vein. If the caliber of the SCIA vessels is too small (less than 1 mm), SIEA vessels may be used as LN flap pedicle vessels. The lymphatic tissue from the groin is then placed to cover the axillary plexus. The distal edge of the flap is tunneled to reach the proximal brachium and fixed with a single transfixation suture (3-0 Vicryl, Ethicon, GB™). Before wound closure, the Licox catether is placed in the lymphatic flap.

Postoperative Care

Blood perfusion of the LN flap is followed by the Licox catether 3 days postoperatively. All patients are monitored postoperatively for 5 days and discharged between the postoperative days 6 to 7. Suction drainages from the axillary and abdominal wounds are removed when the production is less than 40 ml/day. Manual drainage (physiotherapy) starts on the second postoperative day and recommended three times a week for a month; and 2 times a week up to 2 months after the surgery. Patients use an elastic compression dressing in their symptomatic arm for 6 months. After 6 month all patients dry the end use of compression therapy.

Optionally, the methods of the invention further comprise contacting non-lymph node tissue in the skin flap or skin graft with an agent selected from the group consisting of Vascular Endothelial Growth Factor C (VEGF-C) polynucleotides, VEGF-C polypeptides, Vascular Endothelial Growth Factor D (VEGF-D) polynucleotides, and VEGF-D polypeptides, in an amount effective to reduce edema or increase perfusion at the skin graft or skin flap, thereby improving the healing of the skin graft or skin flap.

The term "VEGF-C polypeptide" includes any polypeptide that has a VEGF-C or VEGF-C analog amino acid sequence (as defined elsewhere herein in greater detail) and that possesses VEGFR-3 binding and stimulatory properties. The term "VEGF-C polynucleotide" includes any polynucleotide (e.g., DNA or RNA, single- or double-stranded) comprising a nucleotide sequence that encodes a VEGF-C polypeptide. Due to the well-known degeneracy of the genetic code, multiple VEGF-C polynucleotide sequences encode any selected VEGF-C polypeptide.

In a preferred embodiment, the VEGF-C polynucleotide for use in a method of the invention is in an adenovirus construct. Preferably, the adenovirus construct is pAdApt. Either hVEGF-C (wild type—SEQ ID NO:1), pre-pro VEGF-C (SEQ ID NO:2) or a C156S mutant of either SEQ ID NO:1 or 2 may be cloned into pAdApt. Preferable, the VEGF-C polynucleotides that are used in the invention are pAdAptVEGF-C (SEQ ID NO: 5)

As described below in greater detail, the improvements to surgical skin graft/skin flap procedures (or to isolated tissue containing a lymph node or a lymph node fragment) described herein are applicable to a wide variety of surgeries. For example, in one variation, the underlying tissue is breast tissue. In a preferred embodiment, the skin graft or skin flap is attached in a breast augmentation, breast reduction, mastopexy, or gynecomastia procedure.

In one embodiment, the surgery is a cosmetic surgery procedure. In a preferred embodiment, the cosmetic surgery is a facial cosmetic surgery procedure selected from the group consisting of rhytidectomy, browlift, otoplasty, blepharoplasty, rhinoplasty, facial implant, and hair replacement therapy. In another embodiment, the surgery is a reconstructive surgery. In a preferred embodiment, the reconstructive surgery corrects a congenital defect selected from the group consisting of birthmark, cleft palate, cleft lip, syndactyly, urogenital and anorectal malformations, craniofacial birth defects, ear and nasal deformities, and vaginal agenesis. In another preferred embodiment, the reconstructive surgery corrects a defect from an injury, infection, or disease. In yet another preferred embodiment, the reconstructive surgery corrects damage from a burn or skin cancer (or skin cancer related treatment). In another preferred embodiment, the reconstructive surgery is breast reconstruction following mastectomy or injury.

In another embodiment, the invention provides a method of improving the healing of a skin graft or skin flap to underlying tissue of a mammalian subject, comprising contacting skin graft or skin flap tissue or underlying tissue with a composition comprising a healing agent selected from the group consisting of Vascular Endothelial Growth Factor C (VEGF-C) polynucleotides, VEGF-C polypeptides, Vascular Endothelial Growth Factor D (VEGF-D) polynucleotides, and VEGF-D polypeptides. In a preferred embodiment, the healing agent is present in the composition in an amount effective to reduce edema or increase perfusion at the skin graft or skin flap, thereby improving the healing of the skin graft or skin flap.

In another preferred embodiment, the mammalian subject is a human. In another preferred embodiment, the mammalian subject is diabetic.

In a preferred embodiment, the methods of the invention further include a step of attaching the transferred or transplanted tissues, such as the skin graft of skin flap, to the underlying tissue. In one variation, the administering precedes the attaching. Alternatively, the administering occurs subsequent to the attaching. In a preferred variation, the attaching step includes surgical connection of blood vessels between the underlying tissue and the skin graft or skin flap. In one variation, the method further includes contacting the skin graft or skin flap with an angiogenic growth factor. Alternatively, the administering and attaching are performed without use of an angiogenic polypeptide that binds VEGFR-1 or VEGFR-2.

In still another embodiment of the invention provides a method of improving the healing of a skin graft or skin flap to underlying tissue of a mammalian subject wherein the skin graft or skin flap is attached in an abdominoplasty (abdominal lipectomy) or liposuction procedure.

The materials and methods of the invention may be practiced with a skin graft that is a split thickness, full thickness, or composite graft, and/or a skin flap that is a local flap, a regional flap, a musculocutaneous flap, an osteomyocutaneous flap and/or a soft tissue flap. One can also contemplate the use of in vitro epidermal keratinocyte cultures and epidermal sheets formed therefrom into which the VEGF-C and/or VEGF-D polynucleotides have been transfected. The epidermal sheets are administered to a patient, for example, to promote re-epthelialization of burn wounds.

In a further embodiment, the invention provides a method of inhibiting tumor metastases comprising: performing reconstructive surgery following excision of a tumor from a mammalian subject, said surgery including transferring or transplanting a lymph node or lymph node fragment; and administering a composition comprising an agent selected from the group consisting of Vascular Endothelial Growth Factor C (VEGF-C) polynucleotides, VEGF-C polypeptides, Vascular Endothelial Growth Factor D (VEGF-D) polynucleotides, and VEGF-D polypeptides, to a perinodal site that is within 20 cm of the lymph node or lymph node fragment in an amount effective to promote survival of the lymph node and integration of the lymph node into a lymphatic network in the mammalian subject, at the site of transfer or transplantation.

Multiple healing agents are contemplated to be used, alone or in combination, to practice the present invention. In one embodiment, the healing agent comprises a VEGF-C polynucleotide that encodes a VEGF-C polypeptide. In a preferred embodiment, the VEGF-C polynucleotide further encodes a heparin-binding domain in frame with the VEGF-C polypeptide. In a related embodiment, the VEGF-C polypeptide comprises the formula X-B-Z or Z-B-X, wherein X binds Vascular Endothelial Growth Factor Receptor 3 (VEGFR-3) and comprises an amino acid sequence at least 90% identical to a VEGFR-3 ligand selected from the group consisting of (a) the prepro-VEGF-C amino acid sequence set forth in SEQ ID NO: 2; and (b) fragments of (a) that bind VEGFR-3; wherein Z comprises a heparin-binding amino acid sequence; and wherein B comprises a covalent attachment linking X to Z.

In one embodiment, the healing agent comprises a polynucleotide that encodes a polypeptide comprising an amino acid sequence at least 80%, at least 85%, at least 90%, at least 91%, at least 92%, at least 93%, at least 94%, at least 95%, at least 96%, at least 97%, at least 98%, and least 99% or more identical to the amino acid sequence set forth in SEQ ID NO: 2 or to a fragment thereof that binds VEGFR-3, where the polypeptide binds to VEGFR-3.

In another embodiment, the healing agent comprises a polypeptide which comprises an amino acid sequence at least 80%, at least 85%, at least 90%, at least 91%, at least 92%, at least 93%, at least 94%, at least 95%, at least 96%, at least 97%, at least 98%, and least 99% or more identical to the amino acid sequence set forth in SEQ ID NO: 2 or to a fragment thereof that binds VEGFR-3, where the polypeptide binds to VEGFR-3.

In preferred embodiments, the VEGF-C polynucleotide further comprises additional sequences to facilitate the VEGF-C gene therapy. In a preferred embodiment, the polynucleotide further comprises a nucleotide sequence encoding a secretory signal peptide, wherein the sequence encoding the secretory signal peptide is connected in-frame with the sequence that encodes the VEGF-C polypeptide. In a preferred embodiment, the polynucleotide further comprises a promoter and/or enhancer sequence operably connected to the sequence that encodes the secretory signal sequence and VEGF-C polypeptide, wherein the promoter sequence promotes transcription of the sequence that encodes the secretory signal sequence and the VEGF-C polypeptide in cells of the mammalian subject. In one variation, the promoter is a constitutive promoter that promotes expression in a variety of cell types, such as the cytomegalovirus promoter/enhancer. In a highly preferred embodiment, the promoter sequence comprises a skin specific promoter. Preferred promoter sequences include the K14, K5, K6, K16 promoters for the epidermis and alpha 1(I) collagen promoter for the dermis.

Irrespective of which VEGF-C polypeptide is chosen, the VEGF-C polynucleotide preferably comprises a nucleotide sequence encoding a secretory signal peptide fused in-frame with the VEGF-C polypeptide sequence. The secretory signal peptide directs secretion of the VEGF-C polypeptide by the cells that express the polynucleotide, and is cleaved by the cell from the secreted VEGF-C polypeptide. For example, the VEGF-C polynucleotide could encode the complete prepro-VEGF-C sequence set forth in SEQ ID NO: 2 (which includes natural VEGF-C signal peptide); or could encode the VEGF-C signal peptide fused in-frame to a sequence encoding a recombinantly-processed VEGF-C (e.g., amino acids 103-227 of SEQ ID NO: 2) or VEGF-C analog. Moreover, there is no requirement that the signal peptide be derived from VEGF-C. The signal peptide sequence can be that of another secreted protein, or can be a completely synthetic signal sequence effective to direct secretion in cells of the mammalian subject.

In one embodiment, the VEGF-C polynucleotide of the invention comprises a nucleotide sequence that will hybridize to a polynucleotide that is complementary to the human cDNA sequence specified in SEQ ID NO: 1 under the following exemplary stringent hybridization conditions: Hybridization at 42° C. in 50% formamide, 5×SSC, 20 mM Na.PO$_4$, pH 6.8; and washing in 1×SSC at 55° C. for 30 minutes; and wherein the nucleotide sequence encodes a polypeptide that binds and stimulates human VEGFR-2 and/or VEGFR-3. It is understood that variation in these exemplary conditions can be made based on the length and GC nucleotide content of the sequences to be hybridized. Formulas standard in the art are appropriate for determining appropriate hybridization conditions.

The polynucleotide may further optionally comprise sequences whose only intended function is to facilitate large-scale production of the vector, e.g., in bacteria, such as a bacterial origin of replication and a sequence encoding a selectable marker. However, in a preferred embodiment, such extraneous sequences are at least partially cleaved off prior to administration to humans according to methods of the invention.

In one embodiment, a "naked" VEGF-C transgene (i.e., a transgene without a viral, liposomal, or other vector to facilitate transfection) is employed for gene therapy. In this embodiment, the VEGF-C polynucleotide preferably comprises a suitable promoter and/or enhancer sequence for expression in the target mammalian cells, the promoter being operatively linked upstream (i.e., 5') of the VEGF-C coding sequence. The VEGF-C polynucleotide also preferably further includes a suitable polyadenylation sequence.

Polynucleotide healing agents preferably are incorporated into a vector to facilitate delivery to target cells in the mammalian host cells, and a variety of vectors can be employed. Thus, in one embodiment, the invention provides a method of improving the healing of a skin graft or skin flap to underlying tissue of a subject wherein the healing agent comprises a gene therapy vector that comprises the VEGF-C polynucleotide. In a preferred embodiment, the gene therapy vector is an adenoviral or adeno-associated viral vector. In a highly preferred embodiment, the vector comprises a replication-deficient adenovirus, the adenovirus comprising the polynucleotide operably connected to a promoter and flanked by adenoviral polynucleotide sequences. The adenoviral vector should be included in the composition at a titer conducive to promoting healing according to the invention. In an embodiment where the VEGF-C transgene is administered in an adenovirus vector, the vector is preferably administered in a pharmaceutically acceptable carrier at a titer of $10^7$-$10^{13}$ viral particles, and more preferably at a titer of $10^9$-$10^{11}$ viral particles. The adenoviral vector composition preferably is infused over a period of 15 seconds to 30 minutes, more preferably 1 to 10 minutes.

The invention is not limited to a particular vector because a variety of vectors are suitable to introduce the VEGF-C transgene into the host. Exemplary vectors that have been described in the literature include replication-deficient retroviral vectors, including but not limited to lentivirus vectors; adeno-associated viral vectors; adenoviral vectors; lipofectin-mediated gene transfer (BRL); liposomal vectors; and combinations thereof. Additionally, the VEGF-C transgene can be transferred via particle-mediated gene transfer.

In embodiments employing a viral vector, preferred polynucleotides include a suitable promoter and polyadenylation sequence as described herein. The polynucleotide further includes vector polynucleotide sequences (e.g., adenoviral polynucleotide sequences) operably connected to the sequence encoding a VEGF-C polypeptide.

Thus, in one embodiment, the composition to be administered comprises a vector, wherein the vector comprises the VEGF-C polynucleotide. In a preferred embodiment, the vector is an adenovirus vector. In a highly preferred embodiment, the adenovirus vector is replication-deficient, i.e., it cannot replicate in the mammalian subject due to deletion of essential viral-replication sequences from the adenoviral genome. For example, the inventors contemplate a method wherein the vector comprises a replication-deficient adenovirus, the adenovirus comprising the VEGF-C polynucleotide operably connected to a promoter and flanked on either end by adenoviral polynucleotide sequences.

In one embodiment, the healing agent comprises a VEGF-C polypeptide. In a preferred embodiment, the VEGF-C polypeptide comprises a mammalian VEGF-C polypeptide. In a highly preferred embodiment, especially for treatment of humans, the VEGF-C polypeptide comprises a human VEGF-C polypeptide. By "human VEGF-C" is meant a polypeptide corresponding to a naturally occurring protein (prepro-protein, partially-processed protein, or fully-processed mature protein) encoded by any allele of the human VEGF-C gene, or a polypeptide comprising a biologically active fragment of a naturally-occurring mature protein. For example, the VEGF-C polypeptide comprises the amino acid sequence set forth in SEQ ID NO: 2 or comprises a fragment thereof that binds to VEGFR-2 and VEGFR-3 and stimulates VEGFR-2 and VEGFR-3 phosphorylation in cells that express these receptors.

A polypeptide comprising amino acids 103-227 of SEQ ID NO: 2 is specifically contemplated. For example, polypeptides having an amino acid sequence comprising a continuous portion of SEQ ID NO: 2, the continuous portion having, as its amino terminus, an amino acid selected from the group consisting of positions 32-111 of SEQ ID NO: 2, and having, as its carboxyl terminus, an amino acid selected from the group consisting of positions 228-419 of SEQ ID NO: 2 are contemplated. As explained elsewhere herein in greater detail, VEGF-C biological activities, especially those mediated through VEGFR-2, increase upon processing of both an amino-terminal and carboxyl-terminal pro-peptide. Thus, an amino terminus selected from the group consisting of positions 102-131 of SEQ ID NO: 2 is preferred, and an amino terminus selected from the group consisting of positions 103-111 of SEQ ID NO: 2 is highly preferred. Likewise, a carboxyl terminus selected from the group consisting of positions 215-227 of SEQ ID NO: 2 is preferred. The term "human VEGF-C" also is intended to encompass polypeptides encoded by allelic variants of the human VEGF-C characterized by the sequences set forth in SEQ ID NOs: 1 & 2.

Moreover, it is within the capabilities of the person skilled in the art to make and use analogs of human VEGF-C (and polynucleotides that encode such analogs) wherein one or more amino acids have been added, deleted, or replaced with other amino acids, especially with conservative replacements, and wherein the receptor binding and stimulating biological activity has been retained. Analogs that retain VEGFR-3 binding and stimulating VEGF-C biological activity are contemplated as VEGF-C polypeptides for use in the present invention. In a preferred embodiment, analogs having 1, 2, 3, 4, 5, 6, 7, 8, 9, 10, 11, 12, 13, 14, 15, 16, 17, 18, 19, 20, 21, 22, 23, 24, or 25 such modifications and that retain VEGFR-3 binding and stimulating VEGF-C biological activity are contemplated as VEGF-C polypeptides for use in the present invention. Polynucleotides encoding such analogs are generated using conventional PCR, site-directed mutagenesis, and chemical synthesis techniques.

In another preferred embodiment the VEGF-C polypeptide selectively binds VEGFR-3. By "selectively binds VEGFR-3" is meant that the polypeptide fails to significantly bind VEGFR-2 and is not proteolytically processed in vivo into a form that shows significant reactivity with VEGFR-2. An exemplary VEGFR-3 specific VEGF-C polypeptide comprises a VEGF-C156X polypeptide (long-form VEGF-C—SEQ ID NO: 5). By "VEGF-C156X polypeptide" is meant an analog wherein the cysteine at position 156 of SEQ ID NO: 2 has been deleted or replaced by another amino acid. A VEGF-C156X polypeptide analog can be made from any VEGF-C polypeptide of the invention that comprises all of SEQ ID NO: 2 or a portion thereof that includes position 156 of SEQ ID NO: 2. Preferably, the VEGF-C156X polypeptide analog comprises a portion of SEQ ID NO: 2 effective to permit binding to VEGFR-3 and has reduced VEGFR-2 binding affinity.

In a preferred embodiment, the VEGF-C polynucleotide is the pAdaptVEGF-C plasmid. The pAdapt sequence is shown in SEQ ID NO: 5. The pAdaptVEGF-C plasmid encodes the long form of human VEGF-C cloned into HindIII/NheI sites of pAdApt (Crucell) vector. The pAdApt vector has the CMV promoter upstream and SV40 polyA signal downstream of the human VEGF-C gene for protein expression constituting the expression cassette and contains Ad5 sequences 1-454 and 3511-6095 flanking the expression cassette. The construction of pAdaptVEGF-C is known in the art.

Still other healing agents besides VEGF-C polypeptide and polynucleotides are contemplated to be used with methods of the present invention. In one embodiment, the healing agent comprises a VEGF-D polypeptide or a polynucleotide that encodes a VEGF-D polypeptide. Such methods are practiced essentially as described herein with respect to VEGF-C-encoding polynucleotides or polypeptides, except that VEGF-D polynucleotides or polypeptides are employed. Thus, for example, the description above relating to the use of promoter sequences, vectors, and the like is equally applicable to VEGF-D polynucleotides. A cDNA and deduced amino acid sequence for prepro-VEGF-D is set forth herein in SEQ ID NOs: 3 and 4.

VEGF-D (SEQ ID NOs: 3 and 4) is initially expressed as a prepro-peptide that undergoes removal of a signal peptide (residues 1-21 of SEQ ID NO: 4) N-terminal (residues 22-92 of SEQ ID NO: 4) and C-terminal (residues 202-354 of SEQ ID NO: 4) proteolytic processing, and forms non-covalently linked dimers. Isolation of a biologically active fragment of VEGF-D designated VEGF-DΔNΔC, is described in International Patent Publication No. WO 98/07832 (PCT/US97/14696), incorporated herein by reference. VEGF-DΔNΔC consists of amino acid residues 93 to 201 of VEGF-D (SEQ ID NO: 4) and binds VEGFR-2 and VEGFR-3. Partially processed forms of VEGF-D bind to VEGFR-3.

In still another embodiment, the aforementioned method is provided wherein the healing agent comprises a VEGF-D polynucleotide that encodes a VEGF-D polypeptide. In one embodiment, the healing agent comprises a VEGF-D polypeptide comprising an amino acid sequence at least at least 80%, at least 85%, at least 90%, at least 91%, at least 92%, at least 93%, at least 94%, at least 95%, at least 96%, at least 97%, at least 98%, and least 99% or more identical to the amino acid sequence set forth in SEQ ID NO: 4 or to a fragment thereof that is effective to bind VEGFR-3, wherein the polypeptide binds to VEGFR-3.

Due to the well-known degeneracy of the genetic code, there exist multiple VEGF-D encoding polynucleotide sequences for any VEGF-D polypeptide, any of which may be employed according to the methods taught herein.

As described herein in detail with respect to VEGF-C, the use of polynucleotides that encode VEGF-D fragments, VEGF-D analogs, VEGF-D allelic and interspecies variants, and the like which bind and stimulate phosphorylation of VEGFR-3 are all contemplated as being encompassed by the present invention.

In one embodiment, the VEGF-D polynucleotide of the invention comprises a nucleotide sequence that will hybridize to a polynucleotide that is complementary to the human VEGF-D cDNA sequence specified in SEQ ID NO: 3 under the following exemplary stringent hybridization conditions: Hybridization at 42° C. in 50% formamide, 5×SSC, 20 mM Na.PO$_4$, pH 6.8; and washing in 1×SSC at 55° C. for 30 minutes; and wherein the nucleotide sequence encodes a polypeptide that binds and stimulates human VEGFR-2 and/or VEGFR-3. It is understood that variation in these exemplary conditions can be made based on the length and GC nucleotide content of the sequences to be hybridized. Formulas standard in the art are appropriate for determining appropriate hybridization conditions. See Sambrook et al., *Molecular Cloning: A Laboratory Manual* (Second ed., Cold Spring Harbor Laboratory Press, 1989) §§9.47-9.51.

The polynucleotide may further optionally comprise sequences whose only intended function is to facilitate large-scale production of the vector, e.g., in bacteria, such as a bacterial origin of replication and a sequence encoding a selectable marker. However, in a preferred embodiment, such extraneous sequences are at least partially cleaved off prior to administration to humans according to methods of the invention.

In one embodiment, a "naked" VEGF-D transgene (i.e., a transgene without a viral, liposomal, or other vector to facilitate transfection) is employed for gene therapy. In this embodiment, the VEGF-C polynucleotide preferably comprises a suitable promoter and/or enhancer sequence for expression in the target mammalian cells, the promoter being operatively linked upstream (i.e., 5') of the VEGF-D coding sequence. The VEGF-D polynucleotide also preferably further includes a suitable polyadenylation sequence (e.g., the SV40 or human growth hormone gene polyadenylation sequence) operably linked downstream (i.e., 3') of the VEGF-D coding sequence.

In one embodiment, the healing agent comprises a VEGF-D polypeptide. In a preferred embodiment, the VEGF-D polypeptide comprises a mammalian VEGF-D polypeptide. In a highly preferred embodiment, especially for treatment of humans, the VEGF-D polypeptide comprises a human VEGF-D polypeptide. By "human VEGF-D" is meant a polypeptide corresponding to a naturally occurring protein (prepro-protein, partially-processed protein, or fully-processed mature protein) encoded by any allele of the human VEGF-D gene, or a polypeptide comprising a biologically active fragment of a naturally-occurring mature protein. For example, the VEGF-D polypeptide comprises the amino acid sequence set forth in SEQ ID NO: 4 or comprises a fragment thereof that binds to VEGFR-2 and VEGFR-3 and stimulates VEGFR-2 and VEGFR-3 phosphorylation in cells that express these receptors.

Moreover, it is within the capabilities of the person skilled in the art to make and use analogs of human VEGF-D (and polynucleotides that encode such analogs) wherein one or more amino acids have been added, deleted, or replaced with other amino acids, especially with conservative replacements, and wherein the receptor binding and stimulating biological activity has been retained. Analogs that retain VEGFR-3 binding and stimulating VEGF-D biological activity are contemplated as VEGF-D polypeptides for use in the present invention. In a preferred embodiment, analogs having 1, 2, 3, 4, 5, 6, 7, 8, 9, 10, 11, 12, 13, 14, 15, 16, 17, 18, 19, 20, 21, 22, 23, 24, or 25 such modifications and that retain VEGFR-3 binding and stimulating VEGF-D biological activity are contemplated as VEGF-D polypeptides for use in the present invention. Polynucleotides encoding such analogs are generated using conventional PCR, site-directed mutagenesis, and chemical synthesis techniques.

Moreover, a treatment regimen comprising the simultaneous administration of VEGF-D protein (to provide immediate therapy to the target vessel) with a VEGF-D transgene (to provide sustained therapy for several days or weeks) is specifically contemplated as a variation of the invention.

Also contemplated as VEGF-C and VEGF-D polypeptides are non-human mammalian or avian VEGF-C and VEGF-D polypeptides and polynucleotides. By "mammalian VEGF-C" or "mammalian VEGF-D" is meant a polypeptide corresponding to a naturally occurring protein (prepro-protein, partially-processed protein, or fully-processed mature protein) encoded by any allele of a VEGF-C or VEGF-D gene of any mammal, or a polypeptide comprising a biologically active fragment of a mature protein.

In one embodiment of the method of the invention, the contacting and attaching are performed without use of an angiogenic polypeptide that binds VEGFR-1 or VEGFR-2.

In another embodiment, the method includes contacting the skin graft or skin flap or underlying tissue with an angiogenic growth factor that promotes blood vessel growth. For example, the method comprises contacting the skin graft or skin flap or underlying tissue with a composition comprising VEGF-C, VEGF-C156S and/or VEGF-D polynucleotide or polypeptide in combination with a VEGF, VEGF-B, VEGF-E, PlGF, Ang-1, EGF, PDGF-A, PDGF-B, PDGF-C, PDGF-D, FGF, TGF-β, and/or IGF, polynucleotide or polypeptide. In a preferred embodiment, the angiogenic growth factor is substantially free of vascular permeability increasing activity.

As an alternative to being included in a pharmaceutical composition of the invention including a first protein, a second protein or a therapeutic agent may be concurrently administered with the first protein (e.g., at the same time, or at differing times provided that therapeutic concentrations of the combination of agents is achieved at the treatment site).

The composition(s) used to practice methods of the invention optionally comprise additional materials besides the healing agent. For example, the composition preferably includes a pharmaceutically acceptable carrier.

In still another variation, endothelial cells, endothelial progenitor cells, smooth muscle cells, or keratinocytes are transfected ex vivo with the VEGF-C transgene, and the transfected cells are administered to the mammalian subject. Also keratinocytes can be transfected (with VEGF-C transgene) in vitro and then administered to the subject. VEGF-C released in vivo from the transfected cells would then attract the endothelial cells on which the VEGF-C receptors are expressed to migrate and make new vessels. Exemplary procedures for seeding a vascular graft with genetically modified endothelial cells are described in U.S. Pat. No. 5,785,965, incorporated herein by reference.

If the mammalian subject is receiving a vascular graft with the skin graft, the VEGF-C transgene-containing composition may be directly applied to the isolated vessel segment prior to its being grafted in vivo.

Administration via one or more intravenous injections subsequent to the surgical procedure also is contemplated. Localization of the VEGF-C polypeptides to the site of the procedure occurs due to expression of VEGF-C receptors on proliferating endothelial cells. Localization is further facilitated by recombinantly expressing the VEGF-C as a fusion polypeptide. Co-administration of VEGF-C polynucleotides and VEGF-C polypeptides also is contemplated.

In another variation, the VEGF-C or VEGF-D is covalently linked to another peptide that modulates localization or biological activity. This is preferably achieved at the polynucleotide level. For example, a polynucleotide sequence that encodes the VEGF-C or VEGF-D growth factor domain is covalently fused to a nucleotide sequence encoding an amino acid sequence that directs the recombinant growth factor distribution to target tissues. For example, a sequence is linked that will influence new vessels to grow along collagenous bundles or on the surface of basal laminae. It is contemplated that numerous protein domains such as collagen or other extracellular matrix binding domains/sequences could be used to direct the distribution of the recombinant growth factor.

In one embodiment, the heparin-binding domain of VEGF or another heparin-binding growth factor is fused to the growth factor domain of VEGF-C. The heparin-binding domain of VEGF fused with the VEGF-C growth factor domain would result in slow release of the VEGF-C growth factor from heparin.

In a related aspect, the invention provides materials and devices for practice of the above-described methods.

For example, further aspects of the invention are materials that are useful for improving the healing of a skin flap or skin graft to underlying tissue. For example, the invention provides the use of a VEGF-C polynucleotide, and/or a VEGF-C polypeptide and/or a VEGF-D polynucleotide and/or a VEGF-D polypeptide for the manufacture of a medicament to improve the healing of a skin flap or skin graft to underlying tissue. Such compositions are summarized above in the discussion of methods of the invention and described in further detail below. In addition to the aforementioned healing agent(s), the composition preferably further includes one or more pharmaceutically acceptable diluents, adjuvants, or carrier substances.

The polynucleotides, polypeptides, vectors, compositions, and the like that are described for use in methods of the invention are themselves intended as aspects of the invention.

The compositions are also presently valuable for veterinary applications. Particularly domestic animals and thoroughbred horses, in addition to humans, are desired patients for such treatment with a composition of the present invention.

Likewise, the invention also provides surgical devices that are used to reduce edema or increase perfusion at the free flap, skin graft or skin flap comprising a VEGF-C polynucleotide, a VEGF-C polypeptide, a VEGF-D polynucleotide, and/or a VEGF-D polypeptide.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. Where protein therapy is described, embodiments involving polynucleotide therapy (using polynucleotides that encode the protein) are specifically contemplated, and the reverse also is true. Where embodiments of the invention are described with respect to VEGF-C, it should be appreciated that analogous embodiments involving VEGF-D are specifically contemplated, including descriptions of how to make variants of wildtype molecules.

In addition to the foregoing, the invention includes, as an additional aspect, all embodiments of the invention narrower in scope in any way than the variations specifically mentioned above. With respect to aspects of the invention described as a genus, all individual species are individually considered separate aspects of the invention. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention. Additional features and variations of the invention will be apparent to those skilled in the art from the entirety of this application, and all such features are intended as aspects of the invention.

DESCRIPTION OF THE SEQUENCE LISTING

Figure 1:
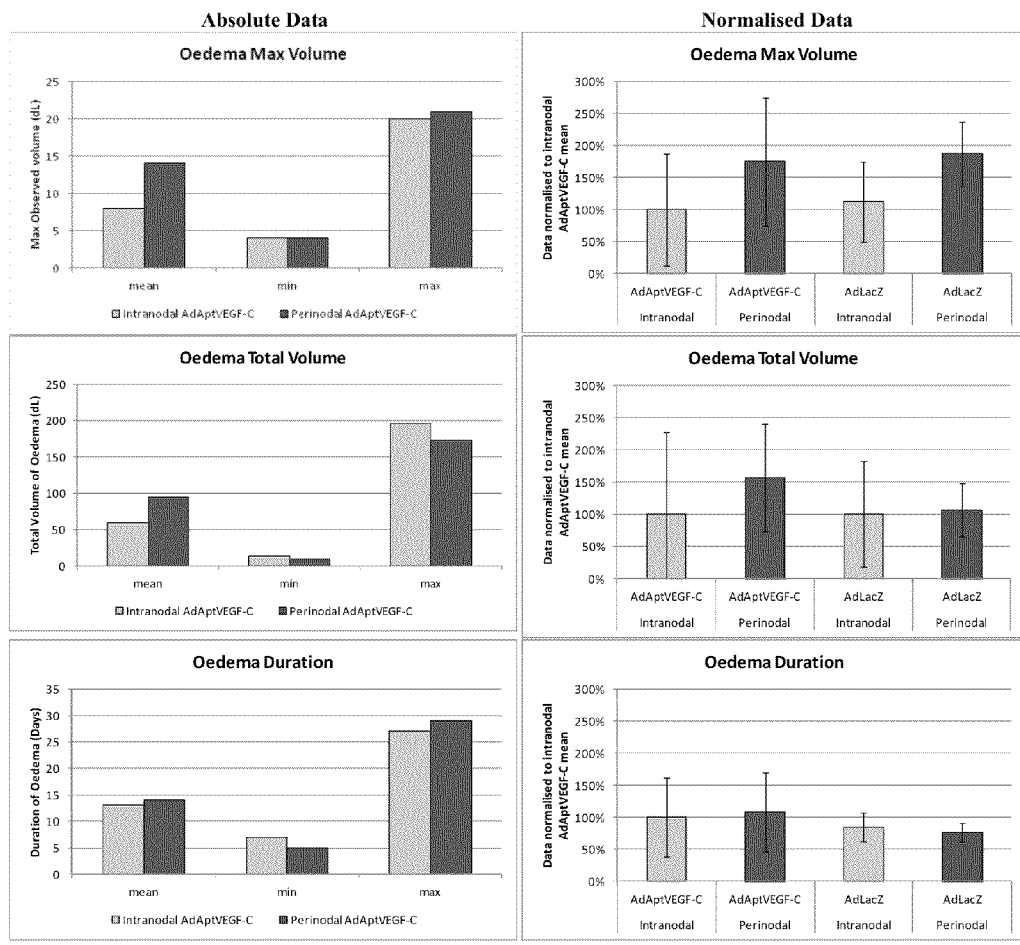
FIG. 1: Comparison of odema accumulation following intranodal or perinodal injection.

SEQ ID NO: 1 is human VEGF-C.
SEQ ID NO: 2 is pre-pro VEGF-C.
SEQ ID NO: 3 is human VEGF-D.
SEQ ID NO: 4 is pre-pro VEGF-D.
SEQ ID NO: 5 is pAdApt VEGF-C.

DETAILED DESCRIPTION

The present invention provides materials, gene transfer methods, and methods to improve healing of skin and/or underlying tissue (tissue with or without a lymph node or lymph node fragment) or adjacent tissues or limbs following a surgical procedure.

1. Vascular Endothelial Growth Factors

Human, non-human mammalian, and avian Vascular Endothelial Growth Factor C (VEGF-C) polynucleotides and polypeptides, as well as VEGF-C variants and analogs, have been described in detail in International Patent Application Number PCT/US98/01973, filed 2 Feb. 1998 and published on 6 Aug. 1998 as International Publication Number WO 98/33917; in PCT Patent Application PCT/FI96/00427, filed Aug. 1, 1996, and published as International Publication WO 97/05250; in related U.S. Pat. Nos. 5,776,755, 6,130,071, 6,221,839, 6,245,530, and 6,361,946, all of which are incorporated herein by reference in their entirety. As explained therein in detail, human VEGF-C is initially produced in human cells as a prepro-VEGF-C polypeptide of 419 amino acids. A cDNA and deduced amino acid sequence for human prepro-VEGF-C are set forth in SEQ ID NOs: 1 and 2, respectively, and a cDNA encoding human VEGF-C has been deposited with the American Type Culture Collection (ATCC), 10801 University Blvd., Manassas, Va. 20110-2209 (USA), pursuant to the provisions of the Budapest Treaty (Deposit date of 24 Jul. 1995 and ATCC Accession Number 97231). VEGF-C sequences from other species have also been reported. See Genbank Accession Nos. MMU73620 (*Mus musculus*); and CCY15837 (*Coturnix coturnix*) for example, incorporated herein by reference.

Moreover, it has been demonstrated that amino acids 103-227 of SEQ ID NO: 2 are not all critical for maintaining VEGF-C functions. A polypeptide consisting of amino acids 113-213 (and lacking residues 103-112 and 214-227) of SEQ ID NO: 2 retains the ability to bind and stimulate VEGF-C receptors, and it is expected that a polypeptide spanning from about residue 131 to about residue 211 will retain VEGF-C biological activity. The cysteine at position 165 of SEQ ID NO: 2 is essential for binding either receptor, whereas analogs lacking the cysteines at positions 83 or 137 compete with native VEGF-C for binding with both receptors and stimulate both receptors.

The cysteine residue at position 156 has been shown to be important for VEGFR-2 binding ability. However, VEGF-C156X polypeptides (i.e., analogs that lack this cysteine due to substitution) remain potent activators of VEGFR-3 and are useful for practice of the present invention.

An alignment of human VEGF-C with VEGF-C from other species (performed using any generally accepted alignment algorithm) suggests additional residues wherein modifications can be introduced (e.g., insertions, substitutions, and/or deletions) without destroying VEGF-C biological activity. Any position at which aligned VEGF-C polypeptides of two or more species have different amino acids, especially different amino acids with side chains of different chemical character, is a likely position susceptible to modification without concomitant elimination of function. An exemplary alignment of human, murine, and quail VEGF-C is set forth in FIG. 5 of PCT/US98/01973.

Apart from the foregoing considerations, it will be understood that innumerable conservative amino acid substitutions can be performed to a wildtype VEGF-C sequence which are likely to result in a polypeptide that retains VEGF-C biological activities, especially if the number of such substitutions is small. By "conservative amino acid substitution" is meant substitution of an amino acid with an amino acid having a side chain of a similar chemical character. Similar amino acids for making conservative substitutions include those having an acidic side chain (glutamic acid, aspartic acid); a basic side chain (arginine, lysine, histidine); a polar amide side chain (glutamine, asparagine); a hydrophobic, aliphatic side chain (leucine, isoleucine, valine, alanine, glycine); an aromatic side chain (phenylalanine, tryptophan, tyrosine); a small side chain (glycine, alanine, serine, threonine, methionine); or an aliphatic hydroxyl side chain (serine, threonine). Addition or deletion of one or a few internal amino acids without destroying VEGF-C biological activities also is contemplated.

Candidate VEGF-C analog polypeptides can be rapidly screened first for their ability to bind and stimulate autophosphorylation of known VEGF-C receptors (VEGFR-2 and VEGFR-3). Polypeptides that stimulate one or both known receptors are rapidly re-screened in vitro for their mitogenic and/or chemotactic activity against cultured capillary or arterial endothelial cells (e.g., as described in WO 98/33917). Polypeptides with mitogenic and/or chemotactic activity are then screened in vivo as described herein for efficacy in methods of the invention. In this way, variants (analogs) of naturally occurring VEGF-C proteins are rapidly screened to determine whether or not the variants have the requisite biological activity to constitute "VEGF-C polypeptides" for use in the present invention.

The growth factor named Vascular Endothelial Growth Factor D (VEGF-D), as well as human sequences encoding VEGF-D, and VEGF-D variants and analogs, have been described in detail in International Patent Application Number PCT/US97/14696, filed 21 Aug. 1997 and published on 26 Feb. 1998 as International Publication Number WO 98/07832; and in U.S. Pat. No. 6,235,713, all of which are incorporated herein by reference in the entirety. As explained therein in detail, human VEGF-D is initially produced in human cells as a prepro-VEGF-D polypeptide of 354 amino acids. A cDNA and deduced amino acid sequence for human prepro-VEGF-D are set forth in SEQ ID NOs: 3 and 4, respectively. VEGF-D sequences from other species also have been reported. See Genbank Accession Nos. D89628 (*Mus musculus*); and AF014827 (*Rattus norvegicus*), for example, incorporated herein by reference.

The prepro-VEGF-D polypeptide has a putative signal peptide of 21 amino acids and is apparently proteolytically processed in a manner analogous to the processing of prepro-VEGF-C. A recombinantly matured VEGF-D lacking residues 1-92 and 202-354 of SEQ ID NO: 4 retains the ability to activate receptors VEGFR-2 and VEGFR-3, and appears to associate as non-covalently linked dimers. Thus, preferred VEGF-D polynucleotides include those polynucleotides that comprise a nucleotide sequence encoding amino acids 93-201 of SEQ ID NO: 4.

2. Reconstructive and Cosmetic Surgery

Reconstructive surgery is generally performed on abnormal structures of the body, caused by birth defects, developmental abnormalities, trauma or injury, infection, tumors, or disease. It is generally performed to improve function, but may also be done to approximate a normal appearance. Cosmetic surgery is performed to reshape normal structures of the body to improve the patient's appearance and self-esteem.

Complications resulting from reconstructive and cosmetic surgery may include infection; excessive bleeding, such as hematomas (pooling of blood beneath the skin); significant bruising and wound-healing difficulties; pain; edema; and problems related to anesthesia and surgery. The methods and compositions described herein provide a much-needed treatment to improve post-surgical wound healing.

Many common reconstructive and cosmetic surgery procedures result in painful swelling and bleeding where skin flaps and/or grafts are used. In breast augmentation, breast reduction, mastopexy and gynecomastia procedures, for example, fluid accumulation and swelling may result, possibly requiring subsequent corrective surgical procedures. In such procedures, skin of and around the nipple is separated and/or removed from the underlying breast tissue. A skin flap or skin graft is frequently necessary to compensate for the change in breast size and/or to gain access to underlying tissues for implantation or reduction. Accordingly, the methods and compositions of the present invention can be used to promote wound healing prior to, during, and/or following the aforementioned surgical procedures.

Similarly, cosmetic surgery procedures such as rhytidectomy, browlift, otoplasty, blepharoplasty, rhinoplasty, facial implant, and hair replacement therapy will also benefit from the present invention. In such procedures, skin is lifted and underlying tissue and muscles are removed or manipulated. A skin flap or skin graft is frequently necessary to compensate for skin tissue loss and/or to gain access to the tissues and muscles beneath the skin. Accordingly, the methods and compositions of the present invention can be used to promote wound healing prior to, during, and/or following the aforementioned surgical procedures.

In an abdominoplasty procedure, the abdomen is flattened by removing excess fat and skin and tightening muscles of the abdominal wall. Bleeding under the skin flap and poor healing resulting in skin loss and scarring may occur, possibly requiring a second operation. Accordingly, the methods and compositions of the present invention can be used to promote wound healing prior to, during, and/or following the aforementioned surgical procedure.

Reconstructive surgery procedures such as those to repair a birthmark, cleft palate, cleft lip, syndactyly, urogenital and anorectal malformations, craniofacial birth defects, ear and nasal deformitites or vaginal agenesis similarly involve incisions and manipulations in skin and underlying tissues for the restoration of body features. A skin flap or skin graft is frequently necessary to compensate for skin tissue loss and/or to gain access to the tissues and muscles beneath the skin. Accordingly, the methods and compositions of the present invention can be used to promote wound healing prior to, during, and/or following the aforementioned surgical procedures.

Similarly, reconstructive surgery to correct defects resulting from an injury such as a burn, infection, or disease such as skin cancer will also benefit from the compositions and methods of the present invention. For example, an oseomyocutaneous flap (a flap containing bone and soft tissue) is often used to reconstruct the skin following skin cancer excision. Thus, the present invention may be employed to reduce the swelling and scarring complications associated with such a procedure.

3. Skin Flaps and Skin Grafts

A flap is a section of living tissue that carries its own blood supply and is moved from one area of the body to another. Flap surgery can restore form and function to areas of the body that have lost skin, fat, muscle movement, and/or skeletal support.

A local flap uses a piece of skin and underlying tissue that lie adjacent to the wound. The flap remains attached at one end so that it continues to be nourished by its original blood supply, and is repositioned over the wounded area. A regional flap uses a section of tissue that is attached by a specific blood vessel. When the flap is lifted, it needs only a very narrow attachment to the original site to receive its nourishing blood supply from the tethered artery and vein. A musculocutaneous flap, also called a muscle and skin flap, is used when the area to be covered needs more bulk and a more robust blood supply. Musculocutaneous flaps are often used in breast reconstruction to rebuild a breast after mastectomy. This type of flap remains "tethered" to its original blood supply. In a bone/soft tissue flap, bone, along with the overlying skin, is transferred to the wounded area, carrying its own blood supply.

Typically, a wound that is wide and difficult or impossible to close directly may be treated with a skin graft. A skin graft is basically a patch of healthy skin that is taken from one area of the body, called the "donor site", and used to cover another area where skin is missing or damaged. There are three basic types of skin grafts.

A split-thickness skin graft, commonly used to treat burn wounds, uses only the layers of skin closest to the surface. A full-thickness skin graft might be used to treat a burn wound that is deep and large, or to cover jointed areas where maximum skin elasticity and movement are needed. As its name implies, a full-thickness (all layers) section of skin from the donor site are lifted. A composite graft is used when the wound to be covered needs more underlying support, as with skin cancer on the nose. A composite graft requires lifting all the layers of skin, fat, and sometimes the underlying cartilage from the donor site.

4. Microvascular Free Flap Transfer

Microvascular free flap transfer generally entails the division and subsequent re-anastomosis of the dominant artery and vein in a tissue, allowing the transplanted tissue to survive. A microvascular bed or free flap is an intact microcirculatory network or bed. Microvascular free flap transfer is the auto-transplantation of composite tissues (known as a free flap) from one anatomic region to another (Blackwell et al., 1997, Head Neck 19: 620-28). As such, microvascular free tissue transfer represents the manipulation and transfer of an intact microcirculatory network or bed. This network can supply a variety of tissues because of its functioning microcirculatory network. This vascular network may be detached from the intact organism and maintained ex vivo, permitting its manipulation or modification without danger of systemic toxicity.

When the expendable microvascular beds are in their normal, native state, they contain all of the distinct, constituent cells that exist within the microcirculation (Krapohl et al., 1998, Plast. Reconstr. Surg. 102: 2388-94; Taylor et al., 1987, Br. J. Plast. Surg. 40: 113-41). Grossly, they consist of large muscular arteries, leading to capacitance arterioles, endothelial lined capillaries, venules, veins and all of the phenotypically distinct cells within them (Siemionow et al., 1998, Ann. Plast. Surg. 41: 275-82, Carroll et al, 2002, Head Neck. 22: 700-13). Importantly, in the native state, they contain all of these cell types in a functional and precisely ordered three-dimensional configuration. In a sense, they have already been "patterned." These expendable microvascular beds provide an ideal, living substrate on which to fabricate a "neo-organ," i.e., a non-naturally occurring vascularized tissue that provides a function of a gland or organ, or that supplements the function of a gland or organ. Since microvascular free flaps contain a single afferent artery and efferent vein they can be reintegrated into the systemic circulation by standard vascular anastomoses.

According to the methods of the invention, a tissue of interest (i.e., microvascular free flap) is harvested as an explant for modification and subsequent reattachment or reanastomosis, e.g., to reconstruct defects following tumor extirpation such as in a mastectomy. In performing microvascular free flap transfer, an intact microcirculatory network or bed is detached. According to a method of the invention, this vascular network is detached from the intact organism for a finite period of time (ex vivo), and undergoes modification, e.g., by protein therapy or genetic modification, and in a certain embodiments, by transfection with a polynucleotide encoding a therapeutic polypeptide.

According to a method of the invention, a selected tissue may be excised ("harvested") by conventional surgical methods known in the art (see, e.g., Petry et al., 1984, Plast. Reconstr. Surg. 74: 410-13; Blackwell et al., 1997, Head Neck 19, 620-28). The surgical procedure results in the removal of skin and subcutaneous tissue associated with blood vessels in a select region of the body. For example, the flap can be a superepigastric ("SE" or lower abdomen/groin) flap and the associated blood vessels can be SE blood vessels of the lower abdomen and groin.

In another aspect of the invention, a composite tissue flap, i.e., a flap composed of bone and skin, muscle and skin, adipose tissue and skin, fascia and muscle, or other such combination known to normally be present in the vertebrate body, is used because it has a greater tolerance for ischemia, allowing for more extensive g manipulation prior to re-anastomosis, including protein or gene therapy of the invention.

Once the flap is excised, the proximal blood vessels that are associated with the flap are clamped. Any technique known in the art can be used to clamp the blood vessels.

The selected tissue is maintained ex vivo by methods for maintaining explants well-known in the art. The tissue is preferably perfused, e.g., the tissue can be wrapped in gauze, a catheter can be placed in a blood vessel associated with the tissue and secured with a suture, and the tissue perfused or infused with physiological saline. In one embodiment, the perfusion is conducted at a cold temperature (for cold ischemia). In other embodiments, perfusion is conducted at room temperature or body temperature. Preferably, the tissue is perfused ex vivo through a catheter at a constant perfusion pressure to flush out blood from the flap vessels. Preferably, the infusions are given at physiologic pressures (80-200 mm Hg), since high pressures cause excessive tissue damage, leading to necrosis of all or part of the flap. In one embodiment, a continuous microperfusion system, such as the one described by Milas et al. (1997, Clinical Cancer Research. 3(12-1): 2197-2203) is used.

In other embodiments, an explanted flap can be maintained for a prolonged period of time by using an immunodeficient host as a recipient.

Using conventional surgical procedures (see e.g., Petry et al., 1984, Plast. Reconstr. Surg. 74: 410-33; Blackwell et al., 1997, Head Neck 19, 620-28), the flap is then reinserted into the patient and re-anastomosed to a section of the circulatory system in the patient. Preferably, the flap is attached non-orthotopically, i.e., it is re-anastomosed to a different area of the patient's circulatory system. For example, a flap may be detached from its supply from the femoral artery, transfected by perfusion, then transplanted to the region of the carotid artery and attached to the carotid arterial system. In another embodiment, the flap is reattached to the blood vessels from which it was excised. Preferably, a splint or other protective device is placed over the operative site after attachment or reanastomosis.

In certain cases, re-implantation of the microvascular free flap may produce a substantial degree of scarring, thus obscuring the viability of the tissue independent from surrounding tissue. If this occurs, methods commonly known in the art, such as separation with silicone sheets, may be utilized to separate a re-implanted microvascular free flap from the host in order to inhibit tissue ingrowth.

In some variations of the invention, explanted microvascular free flaps (or beds) are transfected ex vivo. The microvascular free flaps can comprise tissue that includes, but is not limited to, epithelial tissues (including the epidermis), gastrointestinal tissue; connective tissues (including dermis, tendons, ligaments, cartilage, bone and fat tissues), blood; muscle tissues (including heart and skeletal muscles; nerve tissue (including neurons) and glial cells.

Exemplary microvascular free flaps include a transverse rectus abdominus myocutaneous (TRAM) flap (used for microvascular breast reconstruction. It is based on the deep inferior epigastric vessels); a DIEP flap (An abdominal skin and fascia flap that spares the muscle that is harvested in the TRAM flap. It is often a better choice for a free flap in breast reconstruction because it spares the rectus muscle); radial forearm flap (A flap based on the radial artery, which uses the skin and subcutaneous tissue from the palmar side of the forearm.); scapular/parascapular flaps (skin and fascial flap based on the circumflex scapular vessels); Dorsalis pedis flap (harvested from the dorsum of the foot and based on the first dorsal metatarsal artery and dorsalis pedis artery); lateral arm flap; groin flap (one of the original clinical microvascular transplants, it is based on the superficial circumflex iliac artery); bilateral inferior epigastric artery flap (BIEF) (based on the bilateral superficial inferior epigastric arteries or deep inferior epigastric vessels); deltoid flap; and a superior gluteal flap (based on the superficial and deep branches of the superior gluteal vessels). Exemplary muscle flaps include a rectus flap (based on the deep inferior epigastric vessels); a latissimus flap (based on the subscapular-thoracodorsal vessels); a serratus flap (based on the subscapular-thoracodorsal vessels); a gracillis flap; and an extensor brevis flap.

The microvascular free flaps or beds can also comprise tissue derived from organs or organ systems such as the skeletal system (including bones, cartilage, tendons and ligaments); the muscular system (including smooth and skeletal muscles); the circulatory system (including heart, blood vessels, endothelial cells); the nervous system (including brain, spinal cord and peripheral nerves); the respiratory system (including nose, trachea and lungs); the digestive system (including mouth, esophagus, stomach, small and large intestines); the excretory system (including kidneys, ureters, bladder and urethra); the endocrine system (including hypothalamus, pituitary, thyroid, pancreas and adrenal glands); the reproductive system (including ovaries, oviducts, uterus, vagina, mammary glands, testes, seminal vesicles and penis); the lymphatic and immune systems (including lymph, lymph nodes and vessels, white blood cells, bone marrow, T- and B-cells, macrophage/monocytes, adipoctyes, keratinocytes, pericytes, and reticular cells.

In certain embodiments, the selected tissue is autologous. In other embodiments, the tissue is heterologous.

The choice of donor tissue when planning a free flap necessitates proper planning by the reconstructive microsurgeon. Factors that are considered include (1) size and tissue type characteristics of the area to be reconstructed; (2) location of the area to be reconstructed; (3) pedicle length required to reach an adequate artery and vein in the receiving area; (4) size and type of donor tissue; and (5) donor site deformity.

Autologous lymph node transplantation for lymphedema treatment is a recent microsurgical technique (Bernars et al., Lymphology, 34:84-91, 2001), the results of which have yet to be fully evaluated (Campisi et al., Eur. J. Lymph. Rel. Prob., 10:24-27, 2002). Results of the transplantation of lymph nodes in the rat (Shesol et al., Plast. Reconstr. Surg., 63:817-823, 1979; Becker et al., J. Mal. Vascul., 13:199-122, 1988) and in the dog (Chen et al., Br. J. Plast. Surg., 43:578-586, 1990) have been very encouraging.

The techniques employed for an Autologous lymph node transplantation are generally those as previously described by Becker et al., Ann. Surg., 243:313-315, 2006, incorporated by reference, with the growth factor therapy modification. Briefly, surgical approach of the axillary region of the lymphedematous limb is performed in search of receiving vessels: fibrotic muscular and burned tissue are dissected and adhesions released. Axillary vessels are dissected and the periscapular pedicle is isolated. The circumflex posterior branches are individualized and prepared for microanastomoses.

Next, an incision is performed in the inguinal region. These nodes are dissected, freed, and elevated external to internal at the level of the muscular aponeurosis. The nodes are then harvested with an abundant amount of surrounding fat tissue. Lymph nodes are then transplanted in the axillary receiving site. Artery and vein are anastomosed with the vessels previously prepared, using microsurgical techniques. Alternatively, a "double flap" is utilized. A double flap is harvested from the abdominal wall containing lymph nodes and fat and skin for breast reconstruction.

In a first group of patients, a gene therapy vector containing a VEGF-C transgene, a VEGF-D transgene, or both, is injected into the lymph node immediately before harvesting. In a second group of patients, the gene therapy vector is injected into the lymph node tissue after harvesting and before transplant. In a third group, the gene therapy vector is injected after transplant of the lymph node tissue. Control patients receive no gene therapy.

Long-term results are evaluated according to skin elasticity and existence of infectious disease, decrease or disappearance of the lymphedema assessed by measurements, effects observed on isotopic lymphangiography, and ability to stop or discontinue physiotherapy after six months. Long-term results are also evaluated according to the duration of the lymphedema before surgery and occurrence of downstaging after surgery.

Successful gene therapy is indicated by a measurable improvement of a group of gene therapy patients compared to a control group, e.g., assessed through speed of recovery, reduced lymphedema, improved lymph clearance, subjective reports from patients of comfort or symptoms, etc. Alternatively, successful gene therapy is indicated by survival and incorporation of the transplanted lymph node into a lymphatic network.

The procedures described herein can be repeated using a VEGF-C or VEGF-D protein composition in lieu of, or in addition to, the gene therapy composition. Protein therapy will generally have a more immediate, but also a more transient, effect compared to gene therapy.

Exemplary human patient populations that would benefit from the methods of the present invention include patients with vascular reconstruction and postoperative lymphedema, trauma patients with secondary lymphedema, patients with primary lymphedema, caused by local lymph node hypoplasia, and patients with vulva/uterus/ovarian/testicular carcinoma and post operative lymphedema.

There are a number of patient factors that severely limit the likelihood of successful microvascular free tissue transfer. Age in and of itself may not be important; however, many serious systemic diseases are more often found in patients of advanced age. Severe cardiovascular disease and atherosclerosis may compromise flap vessels. Diabetes impairs wound healing and negatively affects vessel health. Connective tissue disorders may also compromise the cardiovascular system. Prior irradiation, diabetes (well-controlled), method of anastomosis, timing, vein graft, and specific arteries/veins are not felt to contribute to flap failure rate. The effect of nicotine on flap failure is controversial.

Proper care after the surgery requires personnel who understand the basic principles of free flap reconstruction. Pressure in the vicinity of the pedicle (including tracheotomy ties or dressings) is avoided. Supplemental oxygen, or humidified air can cool a superficial flap and inhibit its blood flow.

Hemodynamics and blood volume must be monitored closely. Although scant scientific evidence exists to support an ideal hematocrit in postoperative free flap patients, the consensus among experienced surgeons appears to be somewhere between 27 and 29 (Velanovich et al., American Surgeon 54(11):659-663, 1988). Close surveillance for hematoma formation is necessary to avoid the deadly consequences of vascular compression. Blood pressure should be maintained appropriately.

Pharmacotherapy has become routine in free tissue transfers, and much of the basis is borrowed from organ transplantation data. Aspirin therapy is initiated after the surgery using 5-10 grains daily for 2 to 3 weeks in order to inhibit platelet and endothelial cyclooxygenase. Dextran infusion has also been used for its viscosity-lowering properties and inhibition of rouleaux formation. Despite these properties, studies show no effect on overall flap survival when compared with aspirin. Systemic complications are 3.9-7.2 times more common with dextran infusion. Heparin administration, whether in the form of a 5000U one-time bolus at the time of release of the anastomosis, or as a post-operative drip has little clinical data to support its use. Recently, low-molecular weight heparin has been shown to reduce thrombosis in renal grafts (Alkunaizi et al., Transplantation 1998; 66: 533). Other anticoagulation agents have yet to be evaluated in any large studies.

8-20% of patients undergoing free tissue transfer will develop an infection. The effects of post-operative infection can be serious in the area of a free flap anastomosis. This concern has led to several studies looking at the efficacy of different antibiotic regimes. Prolonged Clindamycin (5 days vs 1) was not shown to effect flap outcome. Topical antibiotics used during the surgical procedure also showed no influence on flap outcome (Simons et al., Laryngoscope. 111(2):329-35, 2001). The literature supports using intravenous antibiotics administered in a fashion similar to other major head and neck procedures. Delirium tremens prophylaxis is also often necessary in this patient population.

Although many different methods of postoperative monitoring exist, the current standard is clinical evaluation. This is accomplished by visually inspecting flap color, turgor and capillary refill; using a hand-held Doppler to evaluate the pedicle frequently during the first 3 days; and performing the prick test daily. A healthy flap will be pink, warm, minimally edematous, and will have a capillary refill time of 1-3 seconds. The prick test will produce 1 to 3 drops of bright red blood. Venous occlusion is indicated by bluish, edematous flap and brisk, dark bleeding on the prick test. Arterial problems produce a pale, cold, flap with no bleeding after pricking.

Early detection of flap compromise allows for earlier intervention, and improved survival. This has led to the development of many different methods of monitoring. Implantable dopplers and flow dopplers have been explored. Temperature measurements have demonstrated reliability, although interference from ambient temperatures in the oral cavity can confound data. Others have used near infra-red spectroscopy to monitor the concentrations of oxy and deoxyhemoglobin. Animal studies indicate accurate measurements through as much as 10 cm of tissue. Transcutaneous and intravascular devices which measure oxygen tension have seen some enthusiasm, but expense continues to be an obstacle. The laser doppler flowmeter also holds promise, but is not applicable to deep flaps or those in the oral cavity. As in many cases in medicine, multiple different solutions to a problem indicate lack of a good solution. Clinical assessment will remain the standard until the expense and reliability problems of the others improve.

5. Gene Therapy Methods

Delivery of a therapeutic composition of the invention to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). Introduction of any one of the polynucleotides of the present invention or a gene encoding the polypeptides of the present invention can also be accomplished with extrachromosomal substrates (transient expression) or artificial chromosomes (stable expression). Transient expression is preferred. Cells may also be cultured ex vivo in the presence of therapeutic compositions of the present invention in order to proliferate or to produce a desired effect on or activity in such cells. Treated cells can then be introduced in vivo for therapeutic purposes. In certain embodiments, a polynucleotide of the present invention or a polynucleotide encoding a therapeutic polypeptide are targeted into the lymph nodes of the microvascular free flap.

6. Routes and Administration

Therapeutic dosing is achieved by monitoring therapeutic benefit in terms of any of the parameters outlined herein (speed of wound healing, reduced edema, reduced complications, etc.) and monitoring to avoid side effects. Preferred dosage provides a maximum localized therapeutic benefit with minimum local or systemic side effects. Side effects to monitor include blood or lymphatic vessel growth and/or fluid build-up in areas outside those being treated, including the heart. Suitable human dosage ranges for the polynucleotides or polypeptides can be extrapolated from these dosages or from similar studies in appropriate animal models. Dosages can then be adjusted as necessary by the clinician to provide maximal therapeutic benefit for human subjects.

The dosage regimen of a protein-containing composition to be used in tissue regeneration will be determined by the attending physician considering various factors which modify the action of the proteins, e.g., amount of tissue weight desired to be formed, the location of the tissue, the condition of the tissue, the size of the tissue area (e.g., size of a wound), type of tissue (e.g., bone), the patient's age, sex, and diet, the severity of any infection, time of administration and other clinical factors. The dosage may vary with the type of matrix used in the reconstitution and with inclusion of other proteins in the composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations, fluorescence microscopy, and tetracycline labeling.

7. Compositions and Formulations

Compositions for use in accordance with the present invention may be formulated in a conventional manner using one or more physiologically acceptable carriers comprising excipients and auxiliaries which facilitate processing of a therapeutic composition into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen.

When a therapeutically effective amount of a composition of the present invention is administered by e.g., intradermal, cutaneous or subcutaneous injection, the composition is preferably in the form of a pyrogen-free, parenterally acceptable aqueous solution. The preparation of such parenterally acceptable protein or polynucleotide solutions, having due regard to pH, isotonicity, stability, and the like, is within the skill in the art. A preferred composition should contain, in addition to protein or other active ingredient of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The composition of the present invention may also contain stabilizers, preservatives, buffers, antioxidants, or other additives known to those of skill in the art. The agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

Optionally, the suspension may also contain suitable stabilizers or agents which increase the solubility of the compositions to allow for the preparation of highly concentrated solutions. Alternatively, the active ingredient may be in powder form for constitution with a suitable vehicle, e.g., sterile pyrogen-free water, before use.

Polypeptides and/or polynucleotides of the invention may be administered in any suitable manner using an appropriate pharmaceutically acceptable vehicle, e.g., a pharmaceutically acceptable diluent, adjuvant, excipient or carrier. The composition to be administered according to methods of the invention preferably comprises (in addition to the polynucleotide or vector) a pharmaceutically acceptable carrier solution such as water, saline, phosphate buffered saline, glucose, or other carriers conventionally used to deliver therapeutics intravascularly. Multi gene therapy is also contemplated, in which case the composition optionally comprises both the polynucleotide of the invention/vector and another polynucleotide/vector selected to inhibit restenosis or other disorder mediated through the action of a VEGF receptor. Exemplary candidate genes/vectors for co transfection with transgenes encoding polypeptides of the invention are described in the literature cited above, including genes encoding cytotoxic factors, cytostatic factors, endothelial growth factors, and smooth muscle cell growth/migration inhibitors.

The "administering" that is performed according to the present method may be performed using any medically-accepted means for introducing a therapeutic directly to a perinodal site, as defined above. The therapeutic composition may be delivered to the patient at multiple sites. The multiple administrations may be rendered simultaneously or may be administered over a period of several hours. In certain cases it may be beneficial to provide a continuous flow of the therapeutic composition. Additional therapy may be administered on a period basis, for example, daily, weekly or monthly. To minimize angiogenic side effects in non-target tissues, preferred methods of administration are methods of local administration, such as administration by intramuscular injection.

The amounts of peptides in a given dosage will vary according to the size of the individual to whom the therapy is being administered as well as the characteristics of the disorder being treated. In exemplary treatments, it may be necessary to administer about 50 mg/day, 75 mg/day, 100 mg/day, 150 mg/day, 200 mg/day, 250 mg/day. These concentrations may be administered as a single dosage form or as multiple doses.

In gene therapy embodiments employing viral delivery, the unit dose may be calculated in terms of the dose of viral particles being administered. Viral doses include a particular number of virus particles or plaque forming units (pfu). For embodiments involving adenovirus, particular unit doses include $10^3, 10^4, 10^5, 10^6, 10^7, 10^8, 10^9, 10^{10}, 10^{11}, 10^{12}, 10^{13}$ or $10^{14}$ pfu. Particle doses may be somewhat higher (10 to 100 fold) due to the presence of infection-defective particles.

The polypeptides may also be employed in accordance with the present invention by expression of such polypeptide in vivo, which is often referred to as gene therapy. The present invention provides a recombinant DNA vector containing a heterologous segment encoding a chimeric polypeptide of the invention that is capable of being inserted into a microorganism or eukaryotic cell and that is capable of expressing the encoded chimeric protein.

In still another variation, endothelial cells or endothelial progenitor cells are transfected ex vivo with the transgene encoding a polypeptide of the invention, and the transfected cells as administered to the mammalian subject. Exemplary procedures for seeding a vascular graft with genetically modified endothelial cells are described in U.S. Pat. No. 5,785,965, incorporated herein by reference.

In preferred embodiments, polynucleotides of the invention further comprises additional sequences to facilitate the gene therapy. In one embodiment, a "naked" transgene encoding a polypeptide of the invention (i.e., a transgene without a viral, liposomal, or other vector to facilitate transfection) is employed for gene therapy. In this embodiment, the polynucleotide of the invention preferably comprises a suitable promoter and/or enhancer sequence (e.g., cytomegalovirus promoter/enhancer [Lehner et al., J. Clin. Microbiol., 29:2494 2502 (1991); Boshart et al., Cell, 41:521 530 (1985)]; *Rous sarcoma* virus promoter [Davis et al., Hum. Gene Ther., 4:151 (1993)]; Tie promoter [Korhonen et al., Blood, 86(5): 1828 1835 (1995)]; or simian virus 40 promoter) for expression in the target mammalian cells, the promoter being operatively linked upstream (i.e., 5') of the polypeptide coding sequence. The polynucleotides of the invention also preferably further includes a suitable polyadenylation sequence (e.g., the SV40 or human growth hormone gene polyadenylation sequence) operably linked downstream (i.e., 3') of the polypeptide coding sequence. The polynucleotides of the invention also preferably comprise a nucleotide sequence encoding a secretory signal peptide fused in frame with the polypeptide sequence. The secretory signal peptide directs secretion of the polypeptide of the invention by the cells that express the polynucleotide, and is cleaved by the cell from the secreted polypeptide. The signal peptide sequence can be that of another secreted protein, or can be a completely synthetic signal sequence effective to direct secretion in cells of the mammalian subject.

The polynucleotide may further optionally comprise sequences whose only intended function is to facilitate large scale production of the vector, e.g., in bacteria, such as a bacterial origin of replication and a sequence encoding a selectable marker. However, in a preferred embodiment, such extraneous sequences are at least partially cleaved off prior to administration to humans according to methods of the invention. One can manufacture and administer such polynucleotides for gene therapy using procedures that have been described in the literature for other transgenes. See, e.g., Isner et al., Circulation, 91: 2687-2692 (1995); and Isner et al., Human Gene Therapy, 7: 989-1011 (1996); incorporated herein by reference in their entirety.

Any suitable vector may be used to introduce the transgene encoding one of the polypeptides of the invention, into the host. Exemplary vectors that have been described in the literature include replication deficient retroviral vectors, including but not limited to *lentivirus* vectors [Kim et al., J. Virol., 72(1): 811-816 (1998); Kingsman & Johnson, Scrip Magazine, October, 1998, pp. 43 46.]; adeno-associated viral vectors [U.S. Pat. No. 5,474,935; U.S. Pat. No. 5,139,941; U.S. Pat. No. 5,622,856; U.S. Pat. No. 5,658,776; U.S. Pat. No. 5,773,289; U.S. Pat. No. 5,789,390; U.S. Pat. No. 5,834,441; U.S. Pat. No. 5,863,541; U.S. Pat. No. 5,851,521; U.S. Pat. No. 5,252,479; Gnatenko et al., J. Investig. Med., 45: 87 98 (1997)]; adenoviral vectors [See, e.g., U.S. Pat. No. 5,792,453; U.S. Pat. No. 5,824,544; U.S. Pat. No. 5,707,618; U.S. Pat. No. 5,693,509; U.S. Pat. No. 5,670,488; U.S. Pat. No. 5,585,362; Quantin et al., Proc. Natl. Acad. Sci. USA, 89: 2581 2584 (1992); Stratford Perricadet et al., J. Clin. Invest., 90: 626 630 (1992); and Rosenfeld et al., Cell, 68: 143 155 (1992)]; an adenoviral adenoassociated viral chimeric (see for example, U.S. Pat. No. 5,856,152) or a *vaccinia* viral or a herpes viral (see for example, U.S. Pat. No. 5,879,934; U.S. Pat. No. 5,849,571; U.S. Pat. No. 5,830,727; U.S. Pat. No. 5,661,033; U.S. Pat. No. 5,328,688; Lipofectin mediated gene transfer (BRL); liposomal vectors [See, e.g., U.S. Pat. No. 5,631,237 (Liposomes comprising Sendai virus proteins)]; and combinations thereof. All of the foregoing documents are incorporated herein by reference in their entirety. Replication deficient adenoviral vectors constitute a preferred embodiment.

Other non-viral delivery mechanisms contemplated include calcium phosphate precipitation (Graham and Van Der Eb, Virology, 52:456-467, 1973; Chen and Okayama, Mol. Cell Biol., 7:2745-2752, 1987; Rippe et al., Mol. Cell Biol., 10:689-695, 1990) DEAE-dextran (Gopal, Mol. Cell Biol., 5:1188-1190, 1985), electroporation (Tur-Kaspa et al., Mol. Cell Biol., 6:716-718, 1986; Potter et al., Proc. Nat. Acad. Sci. USA, 81:7161-7165, 1984), direct microinjection (Harland and Weintraub, J. Cell Biol., 101:1094-1099, 1985.), DNA-loaded liposomes (Nicolau and Sene, Biochim. Biophys. Acta, 721:185-190, 1982; Fraley et al., Proc. Natl. Acad. Sci. USA, 76:3348-3352, 1979; Felgner, Sci Am. 276 (6):102 6, 1997; Felgner, Hum Gene Ther. 7(15):1791 3, 1996), cell sonication (Fechheimer et al., Proc. Natl. Acad. Sci. USA, 84:8463-8467, 1987), gene bombardment using high velocity microprojectiles (Yang et al., Proc. Natl. Acad. Sci USA, 87:9568-9572, 1990), and receptor-mediated transfection (Wu and Wu, J. Biol. Chem., 262:4429-4432, 1987; Wu and Wu, Biochemistry, 27:887-892, 1988; Wu and Wu, Adv. Drug Delivery Rev., 12:159-167, 1993).

The expression construct (or indeed the polypeptides discussed above) may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, In: Liver diseases, targeted diagnosis and therapy using specific receptors and ligands, Wu G, Wu C ed., New York: Marcel Dekker, pp. 87-104, 1991). The addition of DNA to cationic liposomes causes a topological transition from liposomes to optically birefringent liquid-crystalline condensed globules (Radler et al., Science, 275(5301):810 4, 1997). These DNA-lipid complexes are potential non-viral vectors for use in gene therapy and delivery.

Liposome-mediated nucleic acid delivery and expression of foreign DNA in vitro has been successful. Also contemplated in the present invention are various commercial approaches involving "lipofection" technology. In certain embodiments of the invention, the liposome may be complexed with a hemagglutinating virus (HVJ). This has been shown to facilitate fusion with the cell membrane and promote cell entry of liposome-encapsulated DNA (Kaneda et al., Science, 243:375-378, 1989). In other embodiments, the liposome may be complexed or employed in conjunction with nuclear nonhistone chromosomal proteins (HMG-1) (Kato et al., J. Biol. Chem., 266:3361-3364, 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems that can be employed to deliver a nucleic acid encoding a therapeutic gene into cells include receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993, supra).

In other embodiments, the delivery vehicle may comprise a ligand and a liposome. For example, Nicolau et al. (Methods Enzymol., 149:157-176, 1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a particular cell type by any number of receptor-ligand systems with or without liposomes.

In another embodiment of the invention, the expression construct may simply consist of naked recombinant DNA or plasmids. Transfer of the construct may be performed by any of the methods mentioned above that physically or chemically permeabilize the cell membrane. This is applicable particularly for transfer in vitro, however, it may be applied for in vivo use as well. Dubensky et al. (Proc. Nat. Acad. Sci. USA, 81:7529-7533, 1984) successfully injected polyomavirus DNA in the form of CaPO4 precipitates into liver and spleen of adult and newborn mice demonstrating active viral replication and acute infection. Benvenisty and Neshif (Proc. Nat. Acad. Sci. USA, 83:9551-9555, 1986) also demonstrated that direct intraperitoneal injection of CaPO4 precipitated plasmids results in expression of the transfected genes.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., Nature, 327:70-73, 1987). Several devices for accelerating small particles have been developed. One such device relies on a high voltage discharge to generate an electrical current, which in turn provides the motive force (Yang et al., Proc. Natl. Acad. Sci USA, 87:9568-9572, 1990). The microprojectiles used have consisted of biologically inert substances such as tungsten or gold beads.

In embodiments employing a viral vector, preferred polynucleotides still include a suitable promoter and polyadenylation sequence as described above. Moreover, it will be readily apparent that, in these embodiments, the polynucleotide further includes vector polynucleotide sequences (e.g., adenoviral polynucleotide sequences) operably connected to the sequence encoding a polypeptide of the invention.

Thus, in one embodiment the composition to be administered comprises a vector, wherein the vector comprises a polynucleotide of the invention. In a preferred embodiment, the vector is an adenovirus vector. In a highly preferred embodiment, the adenovirus vector is replication deficient, i.e., it cannot replicate in the mammalian subject due to deletion of essential viral replication sequences from the adenoviral genome. For example, the inventors contemplate a method wherein the vector comprises a replication deficient adenovirus, the adenovirus comprising the polynucleotide of the invention operably connected to a promoter and flanked on either end by adenoviral polynucleotide sequences.

Similarly, the invention includes kits which comprise compounds or compositions of the invention packaged in a manner which facilitates their use to practice methods of the invention. In a simplest embodiment, such a kit includes a compound or composition described herein as useful for practice of the invention (e.g., polynucleotides or polypeptides of the invention), packaged in a container such as a sealed bottle or vessel, with a label affixed to the container or included in the package that describes use of the compound or composition to practice the method of the invention. Preferably, the compound or composition is packaged in a unit dosage form. In another embodiment, a kit of the invention includes a composition of both a polynucleotide or polypeptide packaged together with a physical device useful for implementing methods of the invention, such as a stent, a catheter, an extravascular collar, a polymer film, or the like. In another embodiment, a kit of the invention includes compositions of both a polynucleotide or polypeptide of the invention packaged together with a hydrogel polymer, or microparticle polymers, or other carriers described herein as useful for delivery of the polynucleotides or polypeptides to the patient.

The compositions also may comprise suitable solid or gel phase carriers or excipients.

The compositions of the invention may be in the form of a complex of the protein(s) or other active ingredient of present invention along with protein or peptide antigens.

The compositions may include a matrix capable of delivering the protein-containing or other active ingredient-containing composition to the site of tissue damage, providing a structure for the developing bone and cartilage and optimally capable of being resorbed into the body. Such matrices may be formed of materials presently in use for other implanted medical applications. The choice of matrix material is based on biocompatibility, biodegradability, mechanical properties, cosmetic appearance and interface properties.

In further compositions, proteins or other active ingredient of the invention may be combined with other agents beneficial to the treatment of the bone and/or cartilage defect, wound, or tissue in question.

The composition may further contain other agents which either enhance the activity of the protein or other active ingredient or complement its activity or use in treatment. Such additional factors and/or agents may be included in the pharmaceutical composition to produce a synergistic effect with protein or other active ingredient of the invention, or to minimize side effects. VEGF-C and -D proteins form dimers and as a result, pharmaceutical compositions of the invention may comprise a protein of the invention in such multimeric or in complexed forms.

Techniques for formulation and administration of the therapeutic compositions of the instant application may be found in "Remington's Pharmaceutical Sciences," Mack Publishing Co., Easton, Pa., latest edition. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

While the present invention has been described in terms of specific embodiments, it is understood that variations and modifications will occur to those in the art, all of which are intended as aspects of the present invention. Accordingly, only such limitations as appear in the claims should be placed on the invention.

The following Example illustrates the invention:

EXAMPLE 1

Summary

This experiment was devised to compare the efficacy and side-effects of administering VEGF-C via intranodal or perinodal injection.

Abbreviations

VEGF-C Vascular Endothelial Growth Factor C
VEGF-D Vascular Endothelial Growth Factor D
VEGFR-1 Vascular Endothelial Growth Factor Receptor-1
VEGFR-2 Vascular Endothelial Growth Factor Receptor-2
VEGFR-3 Vascular Endothelial Growth Factor Receptor-3
vp viral particles
Lymfactin AdAptVEGF-C Details of Study Methods Details of the studies used are given in Table 1

The data used for this comparison was limited to that obtained using:

the AdApt vector for delivery of the VEGF-C gene
a dose of $1\times10^{11}$ vp or $1\times10^{12}$ vp
a duration of ~2 months (49-91 days).

Due to these limitations it should be noted that not all animals treated within a particular study are included in this overview. Also, due to changes in study design, technical error, etc., data are not available for all animals for all criteria assessed; the number of animals from which the data is available for each assessment is given within Table 2 and Table 3.

TABLE 1

Design of studies used for comparison of routes of administration

| Route | Study number | AdAptVEGF-C Batch | Doses | Duration | Animal nos. | Total animals |
|---|---|---|---|---|---|---|
| Intra-nodal | PR11010 | A2 7.2.2008 | $1 \times 10^{11}$ vp | 61 days 91 days | A11 A7 A8 | 1 2 |
| | | | $1 \times 10^{12}$ vp | 61 days | A9 A10 | 2 |
| | | | | | | 5 |

TABLE 1-continued

Design of studies used for comparison of routes of administration

| Route | Study number | AdAptVEGF-C Batch | Doses | Duration | Animal nos. | Total animals |
|---|---|---|---|---|---|---|
| Peri-nodal | PR11011 | LXVC100801 | $1 \times 10^{11}$ vp | 56 days 58 days | A40 A34 A35 A36 A37 | 1 4 |
| | PR11019 | A2 7.2.2008 | $1 \times 10^{11}$ vp | 71 days 49 days | A38 A50 A51 A52 | 1 3 |
| | | | | | | 9 |

Comparison of Intranodal and Perinodal Injection Routes

Accumulation of Oedema Fluid

The mean maximum volume of accumulated oedema fluid is given in Table 2 (note that the fluid was surgically drained if the volume was estimated to be 2 liters or more), with the total volume of oedema fluid accumulated over the post-treatment period, and duration of the seroma. For ease of comparison, the data has also been normalised against the value of the mean result from the intranodally injected animals; the corresponding AdLacZ data is shown for comparison. Both absolute and normalised results are shown in FIGS. 1a-1c.

It can be seen that, although the mean oedema accumulation is slightly higher following perinodal injection, the range of oedema fluid accumulation is very similar for all criteria. Similarly, the normalised data shows that there is no significant difference between treatments for this parameter.

Inflammatory Marker Cells

The number (B cells, dendritic cells and macrophages) and class (T cells) of inflammatory marker cells was assessed in five sections of tissue (see Table 2 for summary data). However, the degree of inter- and intra-animal variability seen means that it is not possible to determine whether there is any difference between routes of administration or between Lymfactin and AdLacZ treatment.

Histology

The relative amount of fat and fibrosis observed in stained sections of the transplanted lymph nodes indicates the degree of maintenance of the lymph node structure and function; the lower the percentage of fat and fibrosis, the greater the preservation of the lymph node architecture.

Figure 2:
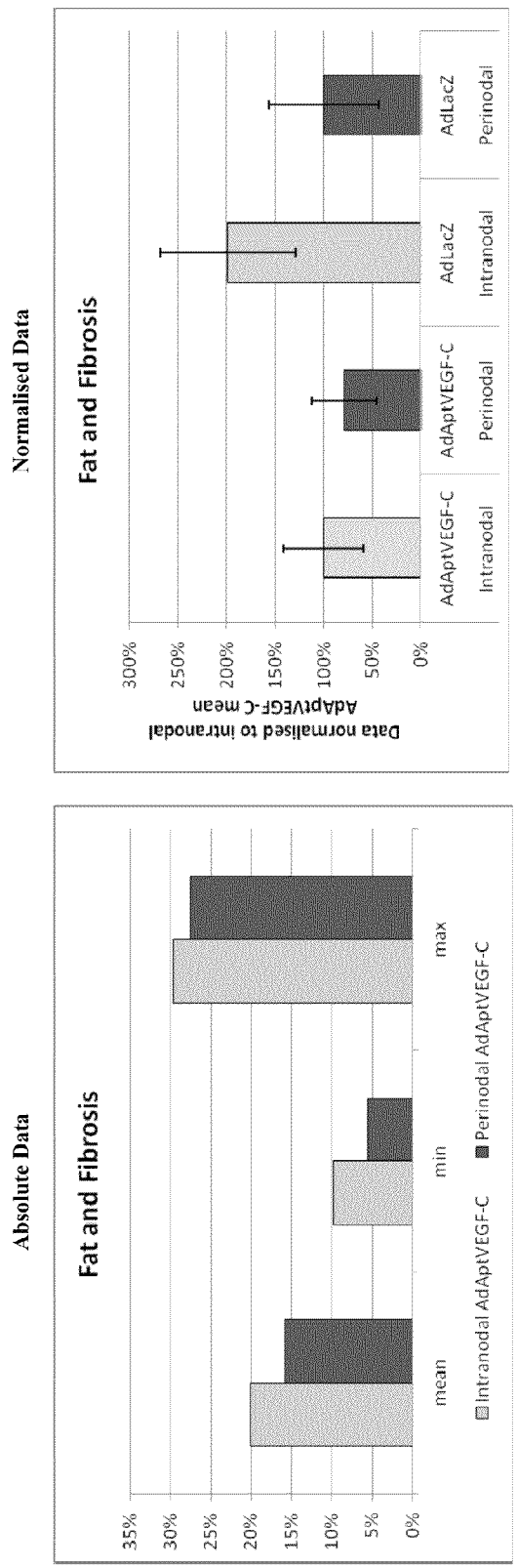
FIG. 2: Comparison of % fat and fibrosis following intranodal or perinodal injection.
Figure 3:
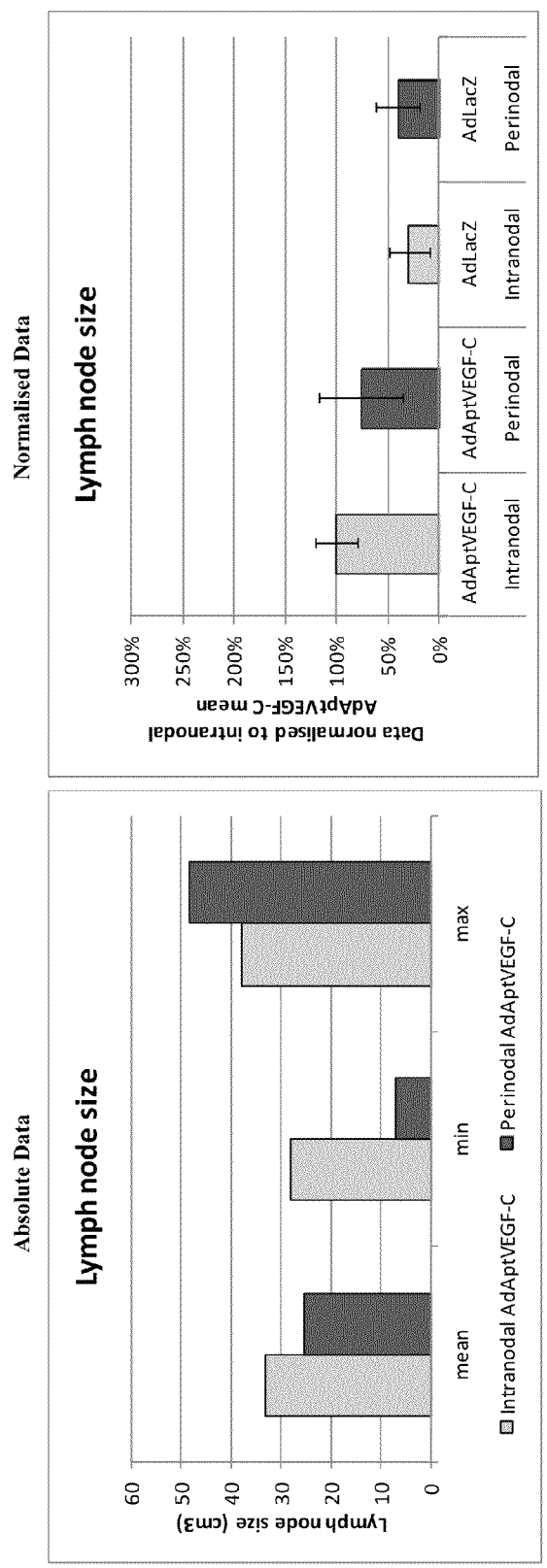
FIG. 3: Comparison of lymph node size following intranodal or perinodal injection

Although intranodal injection of Lymfactin might be expected to better maintain the architecture of the lymph node, it can be seen from FIG. 2 (see also Table 2) that there is equally good maintenance following perinodal injection of Lymfactin (AdApt VEGF-C).

Although, the percentage of fat and fibrosis is markedly higher in lymph nodes treated with AdLacZ delivered intranodally, the maintenance of structure in the perinodal AdLacZ nodes is not significantly different from the Lymfactin treated nodes. The reason for this is not apparent.

Lymph node histology was also assessed and graded for degree of atrophy (see Table 2) and the results correlated with the percentage fat and fibrosis data.

TABLE 2

Dose, Inflammation and Atrophy

| Route | Dose (×10¹¹ vp) | Duration (days) | Oedema Max vol | Oedema Total vol | Oedema Duration† | Inflammatory Marker Cells B cell count | Inflammatory Marker Cells T cell class | Inflammatory Marker Cells Dendritic cell count | Inflammatory Marker Cells Macrophage cell count | Histology % Fat and Fibrosis | Histology Atrophy grade |
|---|---|---|---|---|---|---|---|---|---|---|---|
| INTRANODAL | | | | | | | | | | | |
| Mean | 4.6 | 73 | 8.0 | 60.1 | 13 | 99 | | 47 | 620 | 20.1% | |
| sd | 4.9 | 16 | 6.3 | 76.5 | 8 | 128 | | 31 | 303 | 8.3% | |
| Mode | | | | | | | 1 | | | | 1 or 2 |
| min | 1 | 61 | 3.5 | 14.3 | 7 | 31 | 1 | 12 | 383 | 9.8% | 0 |
| max | 10 | 91 | 20.0 | 196 | 27 | 327 | 2 | 93 | 1148 | 29.7% | |
| n | 5 | 5 | 5 | 5 | 5 | 5 | 5 | 5 | 5 | 5 | 5 |
| PERINODAL | | | | | | | | | | | |
| Mean | 1 | 56 | 14.4 | 94.3 | 14 | 97 | | 304 | 265 | 15.8% | |
| sd | | 7 | 5.8 | 50.2 | 8 | 94 | | 318 | 97 | 6.6% | |
| Mode | | | | | | | 3 | | | | 1 |
| min | 1 | 49 | 3.5 | 10.0 | 5 | 0 | 1 | 4 | 108 | 5.5% | 0 |
| max | 1 | 71 | 20.5 | 173 | 29 | 270 | 3 | 1011 | 371 | 27.5% | 2 |
| n | 9 | 9 | 9 | 9 | 9 | 9 | S | S | S | | |

† = Last day with non-zero volume estimate

Lymph Node Structure and Function
Lymph Node Size

Although there is an apparent decrease in the mean size of the transplanted nodes following perinodal injection of Lymfactin (see Table 3 and FIG. 2), this difference is not statistically significant and reflects the very small sample size (n=2) for this parameter in the intranodal treatment group. It can, however, be seen from the normalised data, that the size of transplanted lymph nodes is markedly greater following treatment with Lymfactin compared with the control, AdLacZ, treatment.

Number of Lymph Vessels

Figure 4:
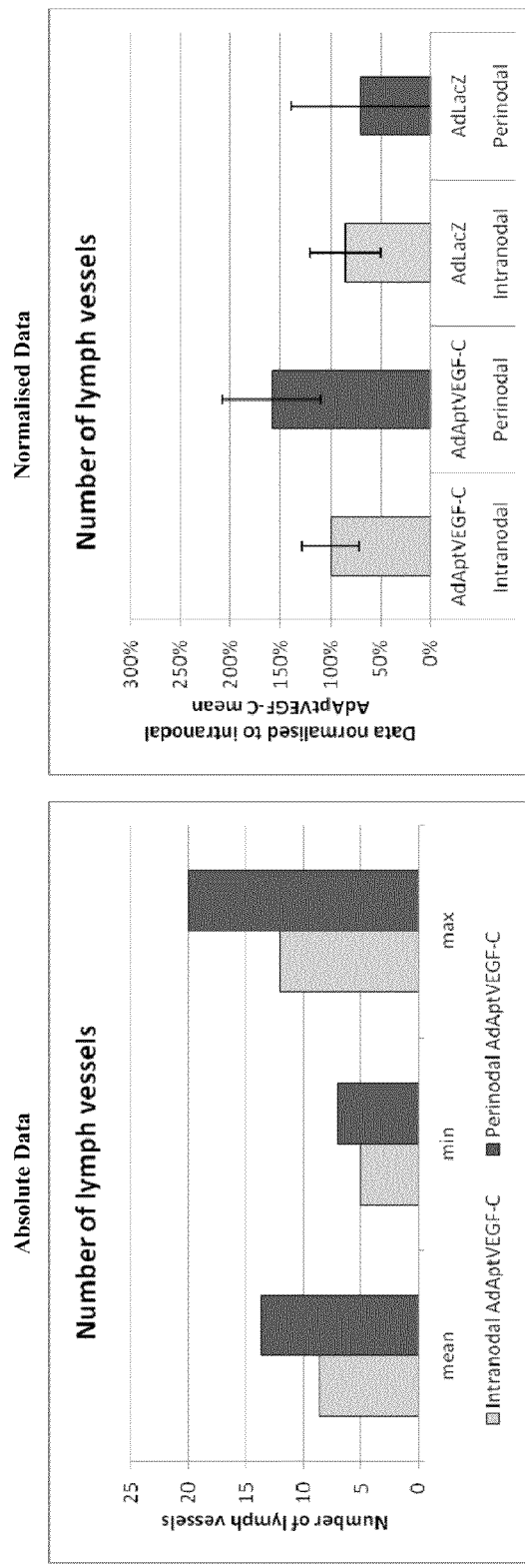
FIG. 4: Comparison of number of lymph vessels following intranodal or pernodal injection.

The number of lymph vessels observed by lymphangiography following treatment via the intranodal or perinodal routes of administration is given in Table 3 and FIG. 4. Treatment with Lymfactin via the perinodal route results in a significantly higher number of lymph vessels than either treatment with perinodal AdLacZ or intranodal Lymfactin ($p<0.01$ and $p<0.05$ respectively, "Student's" unpaired t test). This is as would be predicted, since the amount of adenovirally delivered VEGF-C reaching the tissue surrounding the lymph node should be higher and more consistent following perinodal injection.

Immunohistochemistry
PECAM-1 Positive Capillaries

There was no significant difference between routes of administration in the number of capillaries stained for the endothelial cell marker PECAM-1 (CD31) (see FIG. 5) neither was there any significant difference in the perimeter or area of the stained capillaries (see Table 3).

Figure 5:
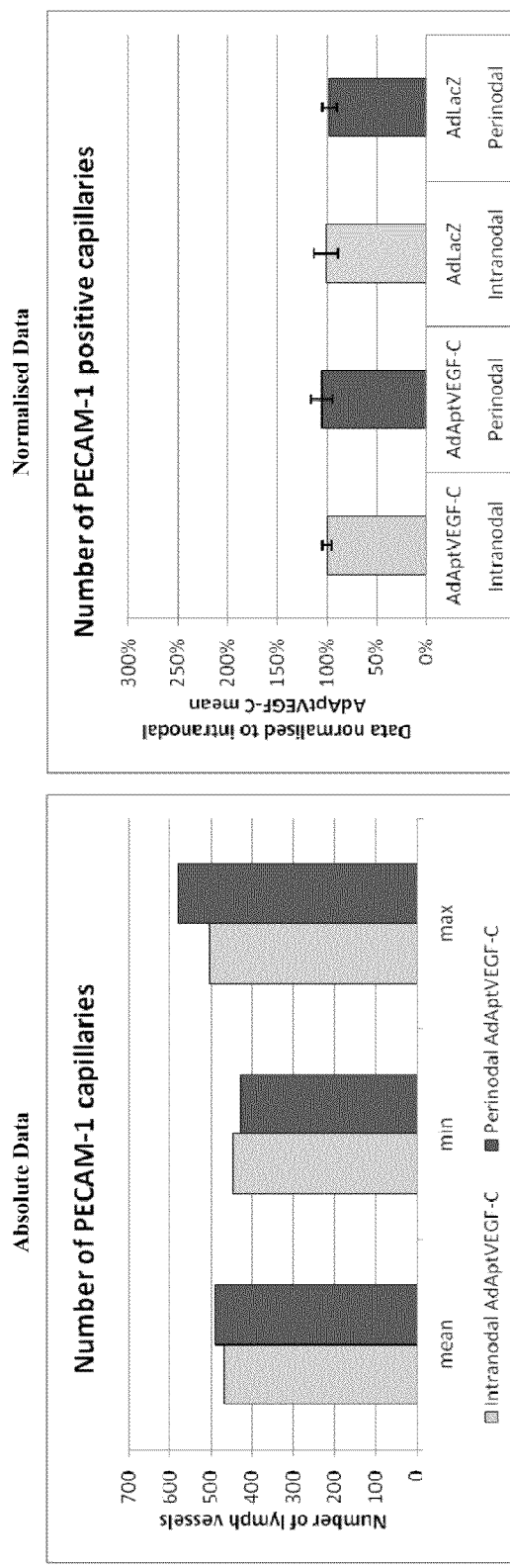
FIG. 5: Comparison of number of PECAM-1 positive capillaries following intranodal or perinodal injection.

There was also no difference between Lymfactin and AdLacZ treated animals in the number of PECAM-1 positive capillaries observed (FIG. 5). However, it is not possible to make a meaningful comparison of the perimeter and area of the capillaries resulting from AdLacZ injection as a different software package was used for the analysis of most of this data.

PROX-1/α-SMA Double Positive Vessels

Figure 6:
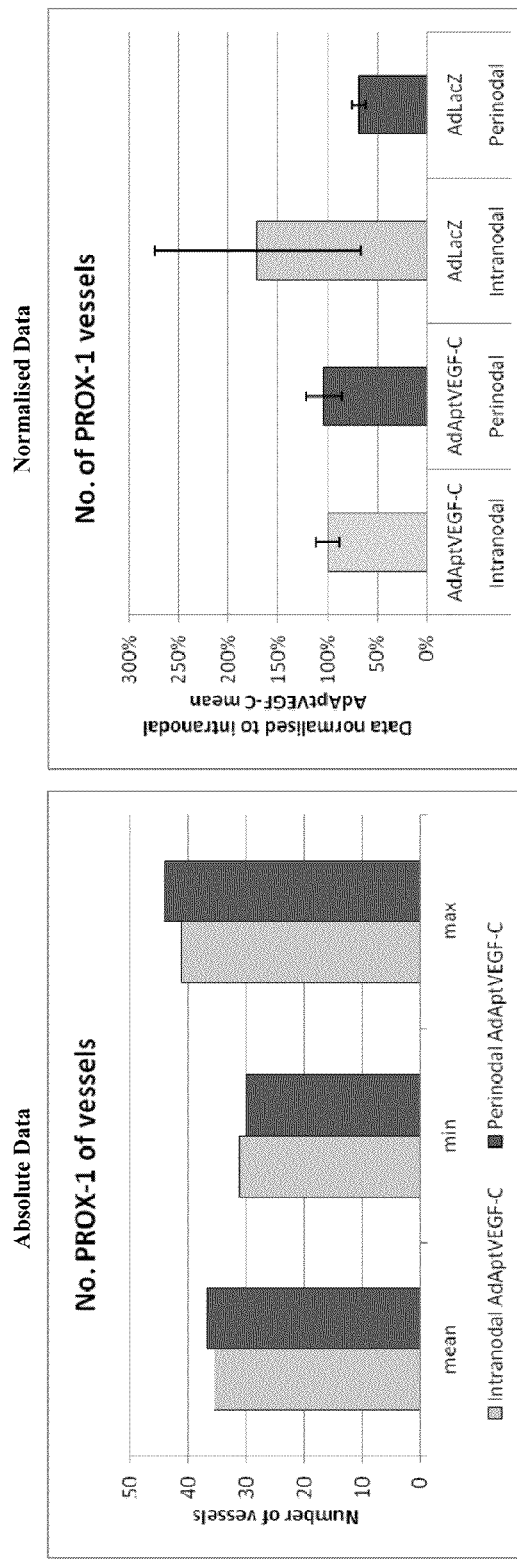

There was no significant difference between routes of administration in the number of vessels stained for the lymphatic endothelial cell marker PROX-1 (see FIG. 6) neither was there any significant difference in the perimeter or area of the stained capillaries (see Table 3).

VEGFR-3 Positive Capillaries

Figure 7:
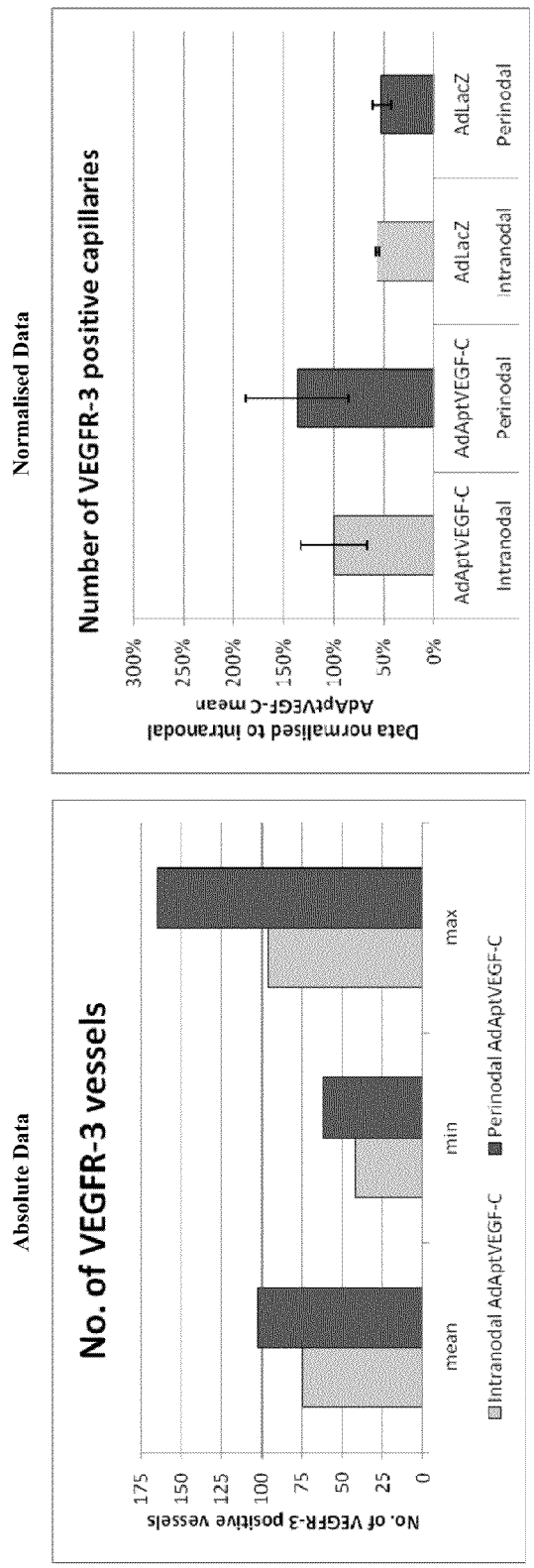

There was no significant difference between routes of administration in the number of vessels stained for the lymphatic endothelial cell marker VEGFR-3 (see FIG. 7) neither was there any significant difference in the perimeter or area of the stained capillaries (see Table 3).

However, the number of VEGFR-3 positive vessels observed in the vicinity of nodes treated with perinodally administered AdLacZ is significantly smaller ($p=0.003$) than in the vicinity of perinodally administered Lymfactin treated nodes. The difference between intranodally administered Lymfactin and AdLacZ is not significant; probably due to the very small number of samples (n=2) for this parameter in the AdLacZ intranodal group. As has already been reported, within study PR11011, i.e. where the analytical software used was comparable, there was also a statistically significant increase in the perimeter and area of VEGFR-3 positive vessels in Lymfactin versus AdLacZ treated animals following perinodal administration.

TABLE 3

| | Lymph node | | Lymph Function | | PECAM-1 positive capillaries | | | PROX-1/a-SMA double positive vessels | | | VEGFR-3 positive capillaries | | |
|---|---|---|---|---|---|---|---|---|---|---|---|---|---|
| Route | Lymph node size | No. of lymph vessels | Patent Blue | Evans Blue | No. | Peri-meter | Area | No. | Peri-meter | Area | No. | Peri-meter | Area |
| INTRANODAL | | | | | | | | | | | | | |
| Mean | 33149 | 9 | 0.099 | 0.139 | 468 | 59 | 194 | 35 | 510 | 435469 | 74 | 266 | 225429 |
| sd | 6896 | 3 | 0.017 | 0.036 | 23 | 2 | 11 | 4 | 41 | 70041 | 25 | 27 | 71891 |
| min | 28272 | 5 | 0.079 | 0.098 | 57 | 57 | 185 | 31 | 462 | 319221 | 42 | 240 | 108538 |
| max | 38025 | 12 | 0.125 | 0.185 | 62 | 62 | 211 | 41 | 557 | 486631 | 96 | 309 | 288031 |
| n | 2 | 5 | 5 | 5 | 5 | 5 | 5 | 5 | 5 | 5 | 5 | 5 | 5 |
| PERINODAL | | | | | | | | | | | | | |
| Mean | 25368 | 14 | 0.161 | 0.197 | 492 | 60 | 197 | 37 | 548 | 553959 | 102 | 209 | 254353 |
| sd | 13469 | 4 | 0.038 | 0.043 | 56 | 3 | 19 | 6 | 31 | 207599 | 38 | 45 | 105249 |
| min | 7018 | 7 | 0.110 | 0.141 | 428 | 56 | 164 | 30 | 507 | 342301 | 62 | 174 | 133247 |
| max | 48576 | 20 | 0.216 | 0.259 | 580 | 64 | 225 | 44 | 582 | 866431 | 165 | 268 | 378759 |
| n | 9 | 9 | 6 | 6 | 9 | 9 | 9 | 5 | 5 | 5 | 5 | 5 | 5 |

Conclusions

No significant differences were seen in the tolerability of Lymfactin or AdLacZ control delivered via either the intranodal or perinodal routes of administration as determined by accumulation of oedema fluid or by inflammatory marker cells.

In terms of efficacy, there was no significant difference in response when Lymfactin was administered perinodally rather than intranodally when assessed by the following criteria: proportion of fat and fibrosis, grade of atrophy, lymph node size, number of lymph vessels observed by lymphangiography, PECAM-1 positive capillaries, or PROX-1/α-SMA double positive vessels. However, the number of VEGFR-3 positive capillaries was significantly greater in the vicinity of transplanted lymph nodes following perinodal administration of Lymfactin than following intranodal Lymfactin.

Lymfactin delivered via the perinodal injection is as well-tolerated, and at least as efficacious as Lymfactin delivered via the intranodal route. This leads to the hypothesis that perinodal administration would be preferred clinically as there are problems associated with intranodal administration.

While the present invention has been described in terms of specific embodiments, it is understood that variations and modifications will occur to those in the art, all of which are intended as aspects of the present invention. Accordingly, only such limitations as appear in the claims should be placed on the invention.

What is claimed is:

1. A method of lymph node transfer comprising:
 transferring or transplanting a lymph node or lymph node fragment in a mammalian subject; and
 administering a composition comprising an agent selected from the group consisting of Vascular Endothelial Growth Factor C (VEGF-C) polynucleotides, VEGF-C polypeptides, Vascular Endothelial Growth Factor D (VEGF-D) polynucleotides, and VEGF-D polypeptides, to a non-lymph node tissue in a perinodal site within 20 cm of the lymph node or lymph node fragment;
 wherein the agent is present in said composition in an amount effective to promote survival of the lymph node and integration of the lymph node into a lymphatic network in the mammalian subject, at the site of transfer or transplantation.

2. A method of treating or inhibiting lymphedema in a mammalian subject comprising:
 performing a surgery on a mammalian subject according to claim 1 that comprises transferring or transplanting a lymph node or lymph node fragment in the mammalian subject according to claim 1 to a site at which the subject is experiencing lymphedema, or is at risk for lymphedema.

3. A method of reducing the incidence or severity of infection associated with a reconstructive surgery comprising:
 performing reconstructive surgery on a mammalian subject, said surgery including transferring or transplanting a lymph node or lymph node fragment; and
 administering a composition comprising an agent selected from the group consisting of Vascular Endothelial Growth Factor C (VEGF-C) polynucleotides, VEGF-C polypeptides, Vascular Endothelial Growth Factor D (VEGF-D) polynucleotides, and VEGF-D polypeptides, to a non-lymph node tissue in a perinodal site within 20 cm of the lymph node or lymph node fragment, in an amount effective to promote survival of the lymph node and integration of the lymph node into a lymphatic network in the mammalian subject, at the site of transfer or transplantation.

4. The method of claim 1 wherein the perinodal site is at a distance of between 0.5 mm and 20 cm from the lymph node or lymph node fragment.

5. The method of claim 1, wherein the perinodal site comprises perinodal fat tissue.

6. The method of claim 1, comprising transferring or transplanting at least one whole lymph node.

7. The method of claim 6, wherein the lymph node or lymph node fragment is isogenic with the mammalian subject.

8. The method of claim 6, wherein the lymph node or lymph node fragment is autologously transferred or transplanted from one location in the subject to another location in the same subject.

9. The method of claim 1, wherein the administering is performed before the transferring or transplanting of the lymph node or lymph node fragment.

10. The method of claim 1, wherein the administering is performed or repeated after surgically removing the lymph node or lymph node fragment from one location and before the transferring or transplanting.

11. The method of claim 1, wherein the administering is performed or repeated after the transferring or transplanting of the lymph node or lymph node fragment.

12. The method of claim 1, wherein the transferring or transplanting comprises transferring or transplanting a skin flap or skin graft in the mammalian subject, wherein the skin flap or skin graft comprises at least one lymph node or lymph node fragment, and the administering is to a perinodal site within the flap, within 20 cm of the lymph node or lymph node fragment.

13. The method of claim 12, wherein the skin flap or skin graft is a microvascular free-flap.

14. The method of claim 12, wherein the composition is administered in an amount effective to reduce edema or increase perfusion at the skin graft or skin flap, thereby improving the healing of the skin graft or skin flap.

15. The method according to any claim 12, wherein the transferring or transplanting comprises a step of attaching the skin graft or skin flap tissue to the underlying tissue.

16. The method according to claim 15, wherein the attaching step includes surgical connection of blood vessels between the underlying tissue and the skin graft or skin flap.

17. The method according to claim 16, wherein the attaching is performed without use of an angiogenic polypeptide that binds VEGFR-1 or VEGFR-2.

18. The method according to claim 12, further comprising contacting the skin graft or skin flap with an angiogenic growth factor.

19. The method according to claim 15, wherein the underlying issue is breast tissue.

20. The method according to claim 19, wherein the skin graft or skin flap is attached in a breast augmentation, breast reduction, mastopexy, or gynecomastia procedure.

21. The method according to claim 12, wherein the skin graft is a split thickness, full thickness, or composite graft; and wherein the skin flap is a local flap, a regional flap, musculocutaneous flap, an osteomyocutaneous flap, or a soft tissue flap.

22. The method according to claim 1, wherein the agent comprises a VEGF-C polynucleotide that encodes a VEGF-C polypeptide.

23. The method according to claim 22, wherein said VEGF-C polynucleotide further encodes a heparin-binding domain in frame with the VEGF-C polypeptide.

24. The method according to claim 22, wherein said polynucleotide further comprises a nucleotide sequence encoding a secretory signal peptide, wherein the sequence encoding the secretory signal peptide is connected in-frame with the sequence that encodes the VEGF-C polypeptide.

25. The method according to claim 24, wherein the polynucleotide further comprises a promoter sequence operably connected to the sequence that encodes the secretory signal sequence and VEGF-C polypeptide, wherein the promoter sequence promotes transcription of the sequence that encodes the secretory signal sequence and the VEGF-C polypeptide in cells of the mammalian subject.

26. The method according to claim 22, wherein the agent comprises a gene therapy vector that comprises the VEGF-C polynucleotide.

27. The method according to claim 26, wherein the gene therapy vector comprises an adenoviral or adeno-associated viral vector.

28. The method according to claim 27, wherein the gene therapy vector is AdApt VEGF-C (SEQ ID NO: 5).

* * * * *

SEQUENCE LISTING

```
<160> NUMBER OF SEQ ID NOS: 5

<210> SEQ ID NO 1
<211> LENGTH: 1997
<212> TYPE: DNA
<213> ORGANISM: Homo sapiens
<220> FEATURE:
<221> NAME/KEY: CDS
<222> LOCATION: (352)..(1608)

<400> SEQUENCE: 1 cccgcccgc ctctccaaaa agctacaccg acgcggaccg cggcggcgtc ctccctcgcc      60
ctcgcttcac ctcgcgggct ccgaatgcgg ggagctcgga tgtccggttt cctgtgaggc     120
ttttacctga cacccgccgc ctttccccgg cactggctgg gagggcgccc tgcaaagttg     180
ggaacgcgga gccccggacc cgctcccgcc gcctccggct cgcccagggg gggtcgccgg     240
gaggagcccg ggggagaggg accaggaggg gcccgcggcc tcgcaggggc gcccgcgccc     300 ccaccctgc ccccgccagc ggaccggtcc cccaccccg gtccttccac c atg cac       357
                                                      Met His
                                                        1 ttg ctg ggc ttc ttc tct gtg gcg tgt tct ctg ctc gcc gct gcg ctg      405
Leu Leu Gly Phe Phe Ser Val Ala Cys Ser Leu Leu Ala Ala Ala Leu
            5                  10                  15 ctc ccg ggt cct cgc gag gcg ccc gcc gcc gcc gcc ttc gag tcc          453
```

```
                  Leu Pro Gly Pro Arg Glu Ala Pro Ala Ala Ala Ala Phe Glu Ser
                      20              25                  30 gga ctc gac ctc tcg gac gcg gag ccc gac gcg ggc gag gcc acg gct      501
Gly Leu Asp Leu Ser Asp Ala Glu Pro Asp Ala Gly Glu Ala Thr Ala
35                  40                  45                  50 tat gca agc aaa gat ctg gag gag cag tta cgg tct gtg tcc agt gta      549
Tyr Ala Ser Lys Asp Leu Glu Glu Gln Leu Arg Ser Val Ser Ser Val
                    55                  60                  65 gat gaa ctc atg act gta ctc tac cca gaa tat tgg aaa atg tac aag      597
Asp Glu Leu Met Thr Val Leu Tyr Pro Glu Tyr Trp Lys Met Tyr Lys
                70                  75                  80 tgt cag cta agg aaa gga ggc tgg caa cat aac aga gaa cag gcc aac      645
Cys Gln Leu Arg Lys Gly Gly Trp Gln His Asn Arg Glu Gln Ala Asn
            85                  90                  95 ctc aac tca agg aca gaa gag act ata aaa ttt gct gca gca cat tat      693
Leu Asn Ser Arg Thr Glu Glu Thr Ile Lys Phe Ala Ala Ala His Tyr
        100                 105                 110 aat aca gag atc ttg aaa agt att gat aat gag tgg aga aag act caa      741
Asn Thr Glu Ile Leu Lys Ser Ile Asp Asn Glu Trp Arg Lys Thr Gln
115                 120                 125                 130 tgc atg cca cgg gag gtg tgt ata gat gtg ggg aag gag ttt gga gtc      789
Cys Met Pro Arg Glu Val Cys Ile Asp Val Gly Lys Glu Phe Gly Val
                    135                 140                 145 gcg aca aac acc ttc ttt aaa cct cca tgt gtg tcc gtc tac aga tgt      837
Ala Thr Asn Thr Phe Phe Lys Pro Pro Cys Val Ser Val Tyr Arg Cys
                150                 155                 160 ggg ggt tgc tgc aat agt gag ggg ctg cag tgc atg aac acc agc acg      885
Gly Gly Cys Cys Asn Ser Glu Gly Leu Gln Cys Met Asn Thr Ser Thr
            165                 170                 175 agc tac ctc agc aag acg tta ttt gaa att aca gtg cct ctc tct caa      933
Ser Tyr Leu Ser Lys Thr Leu Phe Glu Ile Thr Val Pro Leu Ser Gln
        180                 185                 190 ggc ccc aaa cca gta aca atc agt ttt gcc aat cac act tcc tgc cga      981
Gly Pro Lys Pro Val Thr Ile Ser Phe Ala Asn His Thr Ser Cys Arg
195                 200                 205                 210 tgc atg tct aaa ctg gat gtt tac aga caa gtt cat tcc att att aga     1029
Cys Met Ser Lys Leu Asp Val Tyr Arg Gln Val His Ser Ile Ile Arg
                    215                 220                 225 cgt tcc ctg cca gca aca cta cca cag tgt cag gca gcg aac aag acc     1077
Arg Ser Leu Pro Ala Thr Leu Pro Gln Cys Gln Ala Ala Asn Lys Thr
                230                 235                 240 tgc ccc acc aat tac atg tgg aat aat cac atc tgc aga tgc ctg gct     1125
Cys Pro Thr Asn Tyr Met Trp Asn Asn His Ile Cys Arg Cys Leu Ala
            245                 250                 255 cag gaa gat ttt atg ttt tcc tcg gat gct gga gat gac tca aca gat     1173
Gln Glu Asp Phe Met Phe Ser Ser Asp Ala Gly Asp Asp Ser Thr Asp
        260                 265                 270 gga ttc cat gac atc tgt gga cca aac aag gag ctg gat gaa gag acc     1221
Gly Phe His Asp Ile Cys Gly Pro Asn Lys Glu Leu Asp Glu Glu Thr
275                 280                 285                 290 tgt cag tgt gtc tgc aga gcg ggg ctt cgg cct gcc agc tgt gga ccc     1269
Cys Gln Cys Val Cys Arg Ala Gly Leu Arg Pro Ala Ser Cys Gly Pro
                    295                 300                 305 cac aaa gaa cta gac aga aac tca tgc cag tgt gtc tgt aaa aac aaa     1317
His Lys Glu Leu Asp Arg Asn Ser Cys Gln Cys Val Cys Lys Asn Lys
                310                 315                 320 ctc ttc ccc agc caa tgt ggg gcc aac cga gaa ttt gat gaa aac aca     1365
Leu Phe Pro Ser Gln Cys Gly Ala Asn Arg Glu Phe Asp Glu Asn Thr
            325                 330                 335
```

-continued

```
tgc cag tgt gta tgt aaa aga acc tgc ccc aga aat caa ccc cta aat    1413
Cys Gln Cys Val Cys Lys Arg Thr Cys Pro Arg Asn Gln Pro Leu Asn
    340                 345                 350 cct gga aaa tgt gcc tgt gaa tgt aca gaa agt cca cag aaa tgc ttg    1461
Pro Gly Lys Cys Ala Cys Glu Cys Thr Glu Ser Pro Gln Lys Cys Leu
355                 360                 365                 370 tta aaa gga aag aag ttc cac cac caa aca tgc agc tgt tac aga cgg    1509
Leu Lys Gly Lys Lys Phe His His Gln Thr Cys Ser Cys Tyr Arg Arg
                375                 380                 385 cca tgt acg aac cgc cag aag gct tgt gag cca gga ttt tca tat agt    1557
Pro Cys Thr Asn Arg Gln Lys Ala Cys Glu Pro Gly Phe Ser Tyr Ser
            390                 395                 400 gaa gaa gtg tgt cgt tgt gtc cct tca tat tgg aaa aga cca caa atg    1605
Glu Glu Val Cys Arg Cys Val Pro Ser Tyr Trp Lys Arg Pro Gln Met
        405                 410                 415 agc taagattgta ctgttttcca gttcatcgat tttctattat ggaaaactgt         1658
Ser gttgccacag tagaactgtc tgtgaacaga gagacccttg tgggtccatg ctaacaaga    1718 caaaagtctg tctttcctga accatgtgga taactttaca gaaatggact ggagctcatc   1778
tgcaaaaggc ctcttgtaaa gactggtttt ctgccaatga ccaaacagcc aagatttttcc  1838 tcttgtgatt tctttaaaag aatgactata aatttatttt ccactaaaaa tattgtttct   1898
gcattcattt ttatagcaac aacaattggt aaaactcact gtgatcaata tttttatatc   1958
atgcaaaata tgtttaaaat aaaatgaaaa ttgtattat                          1997

<210> SEQ ID NO 2
<211> LENGTH: 419
<212> TYPE: PRT
<213> ORGANISM: Homo sapiens

<400> SEQUENCE: 2

Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
            20                  25                  30

Glu Ser Gly Leu Asp Leu Ser Asp Ala Glu Pro Asp Ala Gly Glu Ala
        35                  40                  45

Thr Ala Tyr Ala Ser Lys Asp Leu Glu Glu Gln Leu Arg Ser Val Ser
    50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190
```

```
Ser Gln Gly Pro Lys Pro Val Thr Ile Ser Phe Ala Asn His Thr Ser
            195                 200                 205

Cys Arg Cys Met Ser Lys Leu Asp Val Tyr Arg Gln Val His Ser Ile
        210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Asp Ala Gly Asp Asp Ser
            260                 265                 270

Thr Asp Gly Phe His Asp Ile Cys Gly Pro Asn Lys Glu Leu Asp Glu
            275                 280                 285

Glu Thr Cys Gln Cys Val Cys Arg Ala Gly Leu Arg Pro Ala Ser Cys
        290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
            355                 360                 365

Cys Leu Leu Lys Gly Lys Lys Phe His His Gln Thr Cys Ser Cys Tyr
        370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser

<210> SEQ ID NO 3
<211> LENGTH: 2029
<212> TYPE: DNA
<213> ORGANISM: Homo sapiens
<220> FEATURE:
<221> NAME/KEY: CDS
<222> LOCATION: (411)..(1475)

<400> SEQUENCE: 3
gttgggttcc agctttctgt agctgtaagc attggtggcc acaccacctc cttacaaagc      60
aactagaacc tgcggcatac attggagaga ttttttttaat tttctggaca tgaagtaaat    120
ttagagtgct ttctaatttc aggtagaaga catgtccacc ttctgattat ttttggagaa    180
cattttgatt tttttcatct ctctctcccc acccctaaga ttgtgcaaaa aaagcgtacc    240
ttgcctaatt gaataatttt cattggattt tgatcagaac tgattatttg gttttctgtg    300
tgaagttttg aggtttcaaa ctttccttct ggagaatgcc ttttgaaaca atttctcta     360 gctgcctgat gtcaactgct agtaatcag tggatattga aatattcaaa atg tac        416
                                                      Met Tyr
                                                        1 aga gag tgg gta gtg gtg aat gtt ttc atg atg ttg tac gtc cag ctg      464
Arg Glu Trp Val Val Val Asn Val Phe Met Met Leu Tyr Val Gln Leu
        5                   10                  15 gtg cag ggc tcc agt aat gaa cat gga cca gtg aag cga tca tct cag      512
Val Gln Gly Ser Ser Asn Glu His Gly Pro Val Lys Arg Ser Ser Gln
    20                  25                  30
```

| | | |
|---|---|---|
| tcc aca ttg gaa cga tct gaa cag cag atc agg gct gct tct agt ttg<br>Ser Thr Leu Glu Arg Ser Glu Gln Gln Ile Arg Ala Ala Ser Ser Leu<br>35                              40                        45                        50 | | 560 |
| gag gaa cta ctt cga att act cac tct gag gac tgg aag ctg tgg aga<br>Glu Glu Leu Leu Arg Ile Thr His Ser Glu Asp Trp Lys Leu Trp Arg<br>                        55                        60                        65 | | 608 |
| tgc agg ctg agg ctc aaa agt ttt acc agt atg gac tct cgc tca gca<br>Cys Arg Leu Arg Leu Lys Ser Phe Thr Ser Met Asp Ser Arg Ser Ala<br>    70                        75                        80 | | 656 |
| tcc cat cgg tcc act agg ttt gcg gca act ttc tat gac att gaa aca<br>Ser His Arg Ser Thr Arg Phe Ala Ala Thr Phe Tyr Asp Ile Glu Thr<br>          85                        90                        95 | | 704 |
| cta aaa gtt ata gat gaa gaa tgg caa aga act cag tgc agc cct aga<br>Leu Lys Val Ile Asp Glu Glu Trp Gln Arg Thr Gln Cys Ser Pro Arg<br>      100                      105                      110 | | 752 |
| gaa acg tgc gtg gag gtg gcc agt gag ctg ggg aag agt acc aac aca<br>Glu Thr Cys Val Glu Val Ala Ser Glu Leu Gly Lys Ser Thr Asn Thr<br>115                            120                        125                        130 | | 800 |
| ttc ttc aag ccc cct tgt gtg aac gtg ttc cga tgt ggt ggc tgt tgc<br>Phe Phe Lys Pro Pro Cys Val Asn Val Phe Arg Cys Gly Gly Cys Cys<br>              135                        140                        145 | | 848 |
| aat gaa gag agc ctt atc tgt atg aac acc agc acc tcg tac att tcc<br>Asn Glu Glu Ser Leu Ile Cys Met Asn Thr Ser Thr Ser Tyr Ile Ser<br>          150                        155                        160 | | 896 |
| aaa cag ctc ttt gag ata tca gtg cct ttg aca tca gta cct gaa tta<br>Lys Gln Leu Phe Glu Ile Ser Val Pro Leu Thr Ser Val Pro Glu Leu<br>              165                        170                        175 | | 944 |
| gtg cct gtt aaa gtt gcc aat cat aca ggt tgt aag tgc ttg cca aca<br>Val Pro Val Lys Val Ala Asn His Thr Gly Cys Lys Cys Leu Pro Thr<br>180                            185                        190 | | 992 |
| gcc ccc cgc cat cca tac tca att atc aga aga tcc atc cag atc cct<br>Ala Pro Arg His Pro Tyr Ser Ile Ile Arg Arg Ser Ile Gln Ile Pro<br>195                            200                        205                        210 | | 1040 |
| gaa gaa gat cgc tgt tcc cat tcc aag aaa ctc tgt cct att gac atg<br>Glu Glu Asp Arg Cys Ser His Ser Lys Lys Leu Cys Pro Ile Asp Met<br>                    215                        220                        225 | | 1088 |
| cta tgg gat agc aac aaa tgt aaa tgt gtt ttg cag gag gaa aat cca<br>Leu Trp Asp Ser Asn Lys Cys Lys Cys Val Leu Gln Glu Glu Asn Pro<br>              230                        235                        240 | | 1136 |
| ctt gct gga aca gaa gac cac tct cat ctc cag gaa cca gct ctc tgt<br>Leu Ala Gly Thr Glu Asp His Ser His Leu Gln Glu Pro Ala Leu Cys<br>          245                        250                        255 | | 1184 |
| ggg cca cac atg atg ttt gac gaa gat cgt tgc gag tgt gtc tgt aaa<br>Gly Pro His Met Met Phe Asp Glu Asp Arg Cys Glu Cys Val Cys Lys<br>260                            265                        270 | | 1232 |
| aca cca tgt ccc aaa gat cta atc cag cac ccc aaa aac tgc agt tgc<br>Thr Pro Cys Pro Lys Asp Leu Ile Gln His Pro Lys Asn Cys Ser Cys<br>275                            280                        285                        290 | | 1280 |
| ttt gag tgc aaa gaa agt ctg gag acc tgc tgc cag aag cac aag cta<br>Phe Glu Cys Lys Glu Ser Leu Glu Thr Cys Cys Gln Lys His Lys Leu<br>                    295                        300                        305 | | 1328 |
| ttt cac cca gac acc tgc agc tgt gag gac aga tgc ccc ttt cat acc<br>Phe His Pro Asp Thr Cys Ser Cys Glu Asp Arg Cys Pro Phe His Thr<br>                    310                        315                        320 | | 1376 |
| aga cca tgt gca agt ggc aaa aca gca tgt gca aag cat tgc cgc ttt<br>Arg Pro Cys Ala Ser Gly Lys Thr Ala Cys Ala Lys His Cys Arg Phe<br>          325                        330                        335 | | 1424 |
| cca aag gag aaa agg gct gcc cag ggg ccc cac agc cga aag aat cct<br>Pro Lys Glu Lys Arg Ala Ala Gln Gly Pro His Ser Arg Lys Asn Pro<br>340                            345                        350 | | 1472 |

```
tga ttcagcgttc caagttcccc atccctgtca tttttaacag catgctgctt    1525
tgccaagttg ctgtcactgt ttttttccca ggtgttaaaa aaaaaatcca ttttacacag    1585
caccacagtg aatccagacc aaccttccat tcacaccagc taaggagtcc ctggttcatt    1645
gatggatgtc ttctagctgc agatgcctct gcgcaccaag gaatggagag gaggggaccc    1705
atgtaatcct tttgtttagt tttgtttttg ttttttggtg aatgagaaag gtgtgctggt    1765
catggaatgg caggtgtcat atgactgatt actcagagca gatgaggaaa actgtagtct    1825
ctgagtcctt tgctaatcgc aactcttgtg aattattctg attctttttt atgcagaatt    1885
tgattcgtat gatcagtact gactttctga ttactgtcca gcttatagtc ttccagttta    1945
atgaactacc atctgatgtt tcatatttaa gtgtatttaa agaaataaaa caccattatt    2005
caagccaaaa aaaaaaaaaa aaaa    2029
```

<210> SEQ ID NO 4
<211> LENGTH: 354
<212> TYPE: PRT
<213> ORGANISM: Homo sapiens

<400> SEQUENCE: 4

```
Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
    50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
    130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270
```

```
Cys Lys Thr Pro Cys Pro Lys Asp Leu Ile Gln His Pro Lys Asn Cys
        275                 280                 285
Ser Cys Phe Glu Cys Lys Glu Ser Leu Glu Thr Cys Cys Gln Lys His
    290                 295                 300
Lys Leu Phe His Pro Asp Thr Cys Ser Cys Glu Asp Arg Cys Pro Phe
305                 310                 315                 320
His Thr Arg Pro Cys Ala Ser Gly Lys Thr Ala Cys Ala Lys His Cys
                325                 330                 335
Arg Phe Pro Lys Glu Lys Arg Ala Ala Gln Gly Pro His Ser Arg Lys
            340                 345                 350
Asn Pro
```

<210> SEQ ID NO 5
<211> LENGTH: 6121
<212> TYPE: DNA
<213> ORGANISM: artificial
<220> FEATURE:
<223> OTHER INFORMATION: Vector

<400> SEQUENCE: 5

```
ttaattaacc gcaattctca tgtttgacag cttatcatca tcaataatat accttatttt      60
ggattgaagc caatatgata atgaggggt ggagtttgtg acgtggcgcg gggcgtggga     120
acggggcggg tgacgtagta gtgtggcgga agtgtgatgt tgcaagtgtg gcggaacaca     180
tgtaagcgac ggatgtggca aaagtgacgt ttttggtgtg cgccggtgta cacaggaagt     240
gacaattttc gcgcggtttt aggcggatgt tgtagtaaat ttgggcgtaa ccgagtaaga     300
tttggccatt ttcgcgggaa aactgaataa gaggaagtga aatctgaata attttgtgtt     360
actcatagcg cgtaatattt gtctagggcc gcggggactt tgaccgttta cgtggagact     420
cgcccaggtg ttttttctcag gtgttttccg cgttccgggt caaagttggc gttttattat     480
tatagtcagt acgtaccagt gcactggcct aggtggtcaa tattggccat tagccatatt     540
attcattggt tatatagcat aaatcaatat tggctattgg ccattgcata cgttgtatcc     600
atatcataat atgtacattt atattggctc atgtccaaca ttaccgccat gttgacattg     660
attattgact agttattaat agtaatcaat tacggggtca ttagttcata gcccatatat     720
ggagttccgc gttacataac ttacggtaaa tggcccgcct ggctgaccgc ccaacgaccc     780
ccgcccattg acgtcaataa tgacgtatgt tcccatagta acgccaatag ggactttcca     840
ttgacgtcaa tgggtggagt atttacggta aactgcccac ttggcagtac atcaagtgta     900
tcatatgcca agtacgcccc ctattgacgt caatgacggt aaatggcccg cctggcatta     960
tgcccagtac atgaccttat gggactttcc tacttggcag tacatctacg tattagtcat    1020
cgctattacc atggtgatgc ggttttggca gtacatcaat gggcgtggat agcggtttga    1080
ctcacgggga tttccaagtc tccaccccat tgacgtcaat gggagtttgt tttggcacca    1140
aaatcaacgg gactttccaa aatgtcgtaa caactccgcc ccattgacgc aaatgggcgg    1200
taggcgtgta cggtgggagg tctatataag cagagctcgt ttagtgaacc gtcagatcgc    1260
ctggagacgc catccacgct gttttgacct ccatagaaga caccgggacc gatccagcct    1320
ccgcggccgg gaacggtgca ttggaagctt ggtaccggtg aattcgctag cgttaacgga    1380
tcctctagac gagatccgaa cttgtttatt gcagcttata atggttacaa ataaagcaat    1440
agcatcacaa atttcacaaa taaagcattt ttttcactgc attctagttg tggtttgtcc    1500
aaactcatca atgtatctta tcatgtctag atctgtactg aaatgtgtgg gcgtggctta    1560
```

| | |
|---|---|
| agggtgggaa agaatatata aggtgggggt cttatgtagt tttgtatctg ttttgcagca | 1620 |
| gccgccgccg ccatgagcac caactcgttt gatggaagca ttgtgagctc atatttgaca | 1680 |
| acgcgcatgc ccccatgggc cggggtgcgt cagaatgtga tgggctccag cattgatggt | 1740 |
| cgccccgtcc tgcccgcaaa ctctactacc ttgacctacg agaccgtgtc tggaacgccg | 1800 |
| ttggagactg cagcctccgc cgccgcttca gccgctgcag ccaccgcccg cgggattgtg | 1860 |
| actgactttg ctttcctgag cccgcttgca agcagtgcag cttcccgttc atccgcccgc | 1920 |
| gatgacaagt tgacggctct tttggcacaa ttggattctt tgacccggga acttaatgtc | 1980 |
| gtttctcagc agctgttgga tctgcgccag caggtttctg ccctgaaggc ttcctcccct | 2040 |
| cccaatgcgg tttaaaacat aaataaaaaa ccagactctg tttggatttg gatcaagcaa | 2100 |
| gtgtcttgct gtctttattt aggggttttg cgcgcgcggt aggcccggga ccagcggtct | 2160 |
| cggtcgttga gggtcctgtg tatttttttcc aggacgtggt aaaggtgact ctggatgttc | 2220 |
| agatacatgg gcataagccc gtctctgggg tggaggtagc accactgcag agcttcatgc | 2280 |
| tgcggggtgg tgttgtagat gatccagtcg tagcaggagc gctgggcgtg gtgcctaaaa | 2340 |
| atgtctttca gtagcaagct gattgccagg ggcaggccct tggtgtaagt gtttacaaag | 2400 |
| cggttaagct gggatgggtg catacgtggg gatatgagat gcatcttgga ctgtatttt | 2460 |
| aggttggcta tgttcccagc catatccctc cggggattca tgttgtgcag aaccaccagc | 2520 |
| acagtgtatc cggtgcactt gggaaatttg tcatgtagct tagaaggaaa tgcgtggaag | 2580 |
| aacttggaga cgcccttgtg acctccaaga ttttccatgc attcgtccat aatgatggca | 2640 |
| atgggcccac gggcggcggc ctgggcgaag atatttctgg gatcactaac gtcatagttg | 2700 |
| tgttccagga tgagatcgtc ataggccatt tttacaaagc gcgggcggag ggtgccagac | 2760 |
| tgcggtataa tggttccatc cggcccaggg gcgtagttac cctcacagat ttgcatttcc | 2820 |
| cacgctttga gttcagatgg ggggatcatg tctacctgcg gggcgatgaa gaaaacggtt | 2880 |
| tccggggtag gggagatcag ctgggaagaa agcaggttcc tgagcagctg cgacttaccg | 2940 |
| cagccggtgg gcccgtaaat cacacctatt accggctgca actggtagtt aagagagctg | 3000 |
| cagctgccgt catccctgag caggggggcc acttcgttaa gcatgtccct gactcgcatg | 3060 |
| ttttccctga ccaaatccgc cagaaggcgc tcgccgccca gcgatagcag ttcttgcaag | 3120 |
| gaagcaaagt ttttcaacgg tttgagaccg tccgccgtag gcatgctttt gagcgtttga | 3180 |
| ccaagcagtt ccaggcggtc ccacagctcg gtcacctgct ctacggcatc tcgatccagc | 3240 |
| atatctcctc gtttcgcggg ttggggcggc tttcgctgta cggcagtagt cggtgctcgt | 3300 |
| ccagacgggc cagggtcatg tctttccacg ggcgcagggt cctcgtcagc gtagtctggg | 3360 |
| tcacggtgaa ggggtgcgct ccgggctgcg cgctggccag ggtgcgcttg aggctggtcc | 3420 |
| tgctggtgct gaagcgctgc cggtcttcgc cctgcgcgtc ggccaggtag catttgacca | 3480 |
| tggtgtcata gtccagcccc tccgcggcgt ggcccttggc gcgcagcttg cccttggagg | 3540 |
| aggcgccgca cgaggggcag tgcagacttt tgagggcgta gagcttgggc gcgagaaata | 3600 |
| ccgattccgg ggagtaggca tccgcgccgc aggccccgca gacggtctcg cattccacga | 3660 |
| gccaggtgag ctctggccgt tcggggtcaa aaaccaggtt tcccccatgc tttttgatgc | 3720 |
| gtttcttacc tctggtttcc atgagccggt gtccacgctc ggtgacgaaa aggctgtccg | 3780 |
| tgtccccgta tacagacttg agaggcctgt cctcgagcgg tgttccgcgg tcctcctcgt | 3840 |
| atagaaactc ggaccactct gagacaaagg ctcgcgtcca ggccagcacg aaggaggcta | 3900 |

```
agtgggaggg gtagcggtcg ttgtccacta gggggtccac tcgctccagg gtgtgaagac    3960
acatgtcgcc ctcttcggca tcaaggaagg tgattggttt gtaggtgtag gccacgtgac    4020
cgggtgttcc tgaaggggg ctataaaagg gggtgggggc gcgttcgtcc tcactctctt    4080
ccgcatcgct gtctgcgagg gccagctgtt ggggtgagtc gacgcgaggc tggatggcct    4140
tccccattat gattcttctc gcttccggcg gcatcgggat gcccgcgttg caggccatgc    4200
tgtccaggca ggtagatgac gaccatcagg gacagcttca aggccagcaa aaggccagga    4260
accgtaaaaa ggccgcgttg ctggcgtttt tccataggct ccgcccccct gacgagcatc    4320
acaaaaatcg acgctcaagt cagaggtggc gaaacccgac aggactataa agataccagg    4380
cgtttccccc tggaagctcc ctcgtgcgct ctcctgttcc gaccctgccg cttaccggat    4440
acctgtccgc ctttctccct tcgggaagcg tggcgctttc tcatagctca cgctgtaggt    4500
atctcagttc ggtgtaggtc gttcgctcca agctgggctg tgtgcacgaa ccccccgttc    4560
agcccgaccg ctgcgcctta tccggtaact atcgtcttga gtccaacccg gtaagacacg    4620
acttatcgcc actggcagca gccactggta acaggattag cagagcgagg tatgtaggcg    4680
gtgctacaga gttcttgaag tggtggccta actacggcta cactagaagg acagtatttg    4740
gtatctgcgc tctgctgaag ccagttacct tcggaaaaag agttggtagc tcttgatccg    4800
gcaaacaaac caccgctggt agcggtggtt tttttgtttg caagcagcag attacgcgca    4860
gaaaaaaagg atctcaagaa gatcctttga tcttttctac ggggtctgac gctcagtgga    4920
acgaaaactc acgttaaggg attttggtca tgagattatc aaaaaggatc ttcacctaga    4980
tccttttaaa ttaaaaatga agttttaaat caatctaaag tatatatgag taaacttggt    5040
ctgacagtta ccaatgctta atcagtgagg cacctatctc agcgatctgt ctatttcgtt    5100
catccatagt tgcctgactc cccgtcgtgt agataactac gatacgggag ggcttaccat    5160
ctggccccag tgctgcaatg ataccgcgag acccacgctc accggctcca gatttatcag    5220
caataaacca gccagccgga agggccgagc gcagaagtgg tcctgcaact ttatccgcct    5280
ccatccagtc tattaattgt tgccgggaag ctagagtaag tagttcgcca gttaatagtt    5340
tgcgcaacgt tgttgccatt gctgcaggca tcgtggtgtc acgctcgtcg tttggtatgg    5400
cttcattcag ctccggttcc caacgatcaa ggcgagttac atgatccccc atgttgtgca    5460
aaaaagcggt tagctccttc ggtcctccga tcgttgtcag aagtaagttg gccgcagtgt    5520
tatcactcat ggttatggca gcactgcata attctcttac tgtcatgcca tccgtaagat    5580
gcttttctgt gactggtgag tactcaacca agtcattctg agaatagtgt atgcggcgac    5640
cgagttgctc ttgcccggcg tcaacacggg ataataccgc gccacatagc agaactttaa    5700
aagtgctcat cattggaaaa cgttcttcgg ggcgaaaact ctcaaggatc ttaccgctgt    5760
tgagatccag ttcgatgtaa cccactcgtg cacccaactg atcttcagca tcttttactt    5820
tcaccagcgt ttctgggtga gcaaaaacag gaaggcaaaa tgccgcaaaa aagggaataa    5880
gggcgacacg gaaatgttga atactcatac tcttcctttt tcaatattat tgaagcattt    5940
atcagggtta ttgtctcatg agcggataca tatttgaatg tatttagaaa aataaacaaa    6000
taggggttcc gcgcacattt ccccgaaaag tgccacctga cgtctaagaa accattatta    6060
tcatgacatt aacctataaa aataggcgta tcacgaggcc ctttcgtctt caagaattgt    6120
t                                                                    6121
```